United States Patent
Matsumoto et al.

(10) Patent No.: US 12,329,552 B2
(45) Date of Patent: Jun. 17, 2025

(54) X-RAY DIAGNOSIS APPARATUS

(71) Applicant: CANON MEDICAL SYSTEMS CORPORATION, Otawara (JP)

(72) Inventors: Masanori Matsumoto, Nasushiobara (JP); Hirona Oikawa, Nasushiobara (JP); Shingo Abe, Nasushiobara (JP); Akio Tetsuka, Shioya-gun (JP); Yoshiyuki Sato, Nasushiobara (JP); Yusuke Kanno, Nasushiobara (JP); Hisayuki Uehara, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 230 days.

(21) Appl. No.: 18/060,324

(22) Filed: Nov. 30, 2022

(65) Prior Publication Data
US 2023/0165548 A1 Jun. 1, 2023

(30) Foreign Application Priority Data
Nov. 30, 2021 (JP) .................................. 2021-194837

(51) Int. Cl.
*A61B 6/00* (2024.01)
*A61B 6/40* (2024.01)
*A61B 6/42* (2024.01)

(52) U.S. Cl.
CPC .............. *A61B 6/4014* (2013.01); *A61B 6/42* (2013.01); *A61B 6/4441* (2013.01); *A61B 6/5247* (2013.01); *A61B 6/547* (2013.01)

(58) Field of Classification Search
CPC ....... A61B 6/00; A61B 6/4014; A61B 6/4441; A61B 6/42; A61B 6/547; A61B 6/5247; A61B 6/541; A61B 6/486; A61B 6/503; A61B 6/5264; A61B 6/46; A61B 5/7292; A61B 5/318
See application file for complete search history.

(56) References Cited

U.S. PATENT DOCUMENTS 7,706,498 B2 * 4/2010 Imai ....................... A61B 6/032
378/20
8,055,045 B2 * 11/2011 Kokubun ............. A61B 6/5264
600/407

(Continued)

FOREIGN PATENT DOCUMENTS

| JP | 2010-274057 A | 12/2010 |
| JP | 2019-136128 A | 8/2019 |
| JP | 2022-93821 A | 6/2022 |

OTHER PUBLICATIONS

Extended European Search Report issued on Apr. 13, 2023 in European Patent Application No. 22210510.8, 7 pages.

*Primary Examiner* — Jurie Yun
(74) *Attorney, Agent, or Firm* — Oblon, McClelland, Maier & Neustadt, L.L.P.

(57) ABSTRACT

According to an embodiment, there is provided that processing circuitry configured to determine a first radiation timing at which a subject is irradiated with an X-ray, based on information on motion of an object in X-ray image data, the information on motion being calculated by the X-ray image data, the X-ray image data being associated with an electrocardiographic waveform of the subject, and repeatedly irradiate the subject with an X-ray at the first radiation timing per cycle of the electrocardiographic waveform of the subject.

18 Claims, 12 Drawing Sheets

(56) References Cited

U.S. PATENT DOCUMENTS

| | | |
|---|---|---|
| 10,736,594 B2 * | 8/2020 | De Man ................. A61B 6/541 |
| 2010/0303323 A1 | 12/2010 | Matsumoto |
| 2011/0201915 A1 | 8/2011 | Gogin et al. |
| 2018/0368798 A1 | 12/2018 | Meyer |
| 2022/0183648 A1 | 6/2022 | Abe et al. |

* cited by examiner

X-RAY DIAGNOSIS APPARATUS

CROSS-REFERENCE TO RELATED APPLICATION

This application is based upon and claims the benefit of priority from Japanese Patent Application No. 2021-194837, filed on Nov. 30, 2021.

FIELD

Embodiments described herein relate generally to an X-ray diagnosis apparatus.

SUMMARY OF INVENTION

An X-ray diagnosis apparatus includes a determiner unit configured to determine a first radiation timing at which a subject is irradiated with an X-ray, based on information on motion of an object in X-ray image data, the information on motion being calculated by the X-ray image data, the X-ray image data being associated with an electrocardiographic waveform of the subject; and an X-ray radiation control unit configured to repeatedly irradiate the subject with an X-ray at the first radiation timing per cycle of the electrocardiographic waveform of the subject.

The X-ray image data may further include a plurality of frames. The determiner unit may determine the first radiation timing based on a magnitude of motion in each of the plurality of frames of the X-ray image data.

The X-ray diagnosis apparatus includes a display control unit configured to display a graph, the electrocardiographic waveform of the subject, and an operative element on a display in association with one another, the graph representing a magnitude of motion in each of frames included in the X-ray image data, the operative element that allows a user to at least either change the first radiation timing or add another radiation timing; and a reception unit configured to receive at least either a change or an addition made by the user with the operative element.

The X-ray diagnosis apparatus includes a display control unit configured to display a plurality of X-ray images based on a plurality of frames included in the X-ray image data and the electrocardiographic waveform of the subject on a display in association with each other; and a reception unit configured to receive at least either a change of the first radiation timing or an addition of another radiation timing made by a user with reference to the electrocardiographic waveform.

The X-ray diagnosis apparatus includes a detector unit configured to detect motion of a device rendered in a plurality of frames included in the X-ray image data on a frame basis, wherein the determiner unit is further configured to determine, as the first radiation timing, a cardiac phase corresponding to a frame exhibiting the device least moving detected by the detector unit among the plurality of frames of the X-ray image data.

The X-ray diagnosis apparatus includes a detector unit configured to detect a change in position of a device rendered in each two chronologically adjacent frames among a plurality of frames included in the X-ray image data, and add the each two chronologically adjacent frames to generate added frames, wherein the determiner unit is further configured to determine, as the first radiation timing, a cardiac phase corresponding to an added frame exhibiting the device least changing in position among the added frames.

The X-ray diagnosis apparatus includes a detector unit configured to detect a change in position of a device rendered in each two frames corresponding to a same cardiac phase of two cycles of the electrocardiographic waveform of the subject among a plurality of frames included in the X-ray image data corresponding to the two cycles, and add the each two frames corresponding to the same cardiac phase to generate added frames, wherein the determiner unit is further configured to determine, as the first radiation timing, a cardiac phase corresponding to an added frame exhibiting the device least changing in position among the added frames.

The X-ray diagnosis apparatus includes the determiner unit is further configured to determine a predetermined number of X-ray radiation timings per cycle of the electrocardiographic waveform of the subject, in addition to the first radiation timing.

The X-ray diagnosis apparatus includes an X-ray detector configured to accumulate and read electric charge in a regular cycle, wherein the determiner unit is further configured to adjust the first radiation timing or another radiation timing in line with a charge accumulation period of the X-ray detector. 10. The X-ray diagnosis apparatus includes the display control unit is further configured to display at least either the graph or the electrocardiographic waveform on the display in association with at least one of the first radiation timing and an end-systolic phase and a mid-diastolic phase of the electrocardiographic waveform.

The X-ray diagnosis apparatus includes the display control unit is further configured to display the electrocardiographic waveform on the display in association with at least one of the first radiation timing and an end-systolic phase and a mid-diastolic phase of the electrocardiographic waveform.

The motion may be motion of a device rendered in each of a plurality of frames included in the X-ray image data.

The motion may be motion of an area containing the tip of a device.

The object may be a wire-shaped device.

The object may be a catheter or a guidewire.

The object includes at least one of a device and a part of subject.

The X-ray images data is captured by X-ray irradiation at the first pulse width, and the X-ray radiation control unit repeatedly irradiate the subject with an X-ray with a second pulse width. Here, the first pulse width is larger than the second pulse width.

The motion may be motion of an area containing the tip of a device.

The information on motion may be calculated by a motion blur of the object.

The information on motion may be calculated by parameters related to a reduction of spatial frequency in X-ray images.

BACKGROUND

Traditionally, an interventional procedure that doctors administer manual procedures to a subject while being irradiated with X-rays for imaging is known. In such an interventional procedure to the heart or a blood vessel surrounding the heart, inserted devices such as a stent and a guide wire appears to move along with the motion of the heart on the screen. In such a case the operator needs to visually follow the motion of the devices, which may be a burden to the operator.

DETAILED DESCRIPTION

According to an embodiment, an X-ray diagnosis apparatus (10) comprising:

a determiner unit (214) configured to determine a first radiation timing at which a subject is irradiated with an X-ray, based on information on motion of an object in X-ray image data, the information on motion being calculated by the X-ray image data, the X-ray image data being associated with an electrocardiographic waveform of the subject; and an X-ray radiation control unit (215) configured to repeatedly irradiate the subject with an X-ray at the first radiation timing per cycle of the electrocardiographic waveform of the subject.

Hereinafter, various embodiments of an X-ray diagnosis apparatus will be described in detail with reference to the accompanying drawings.

First Embodiment

Figure 1:
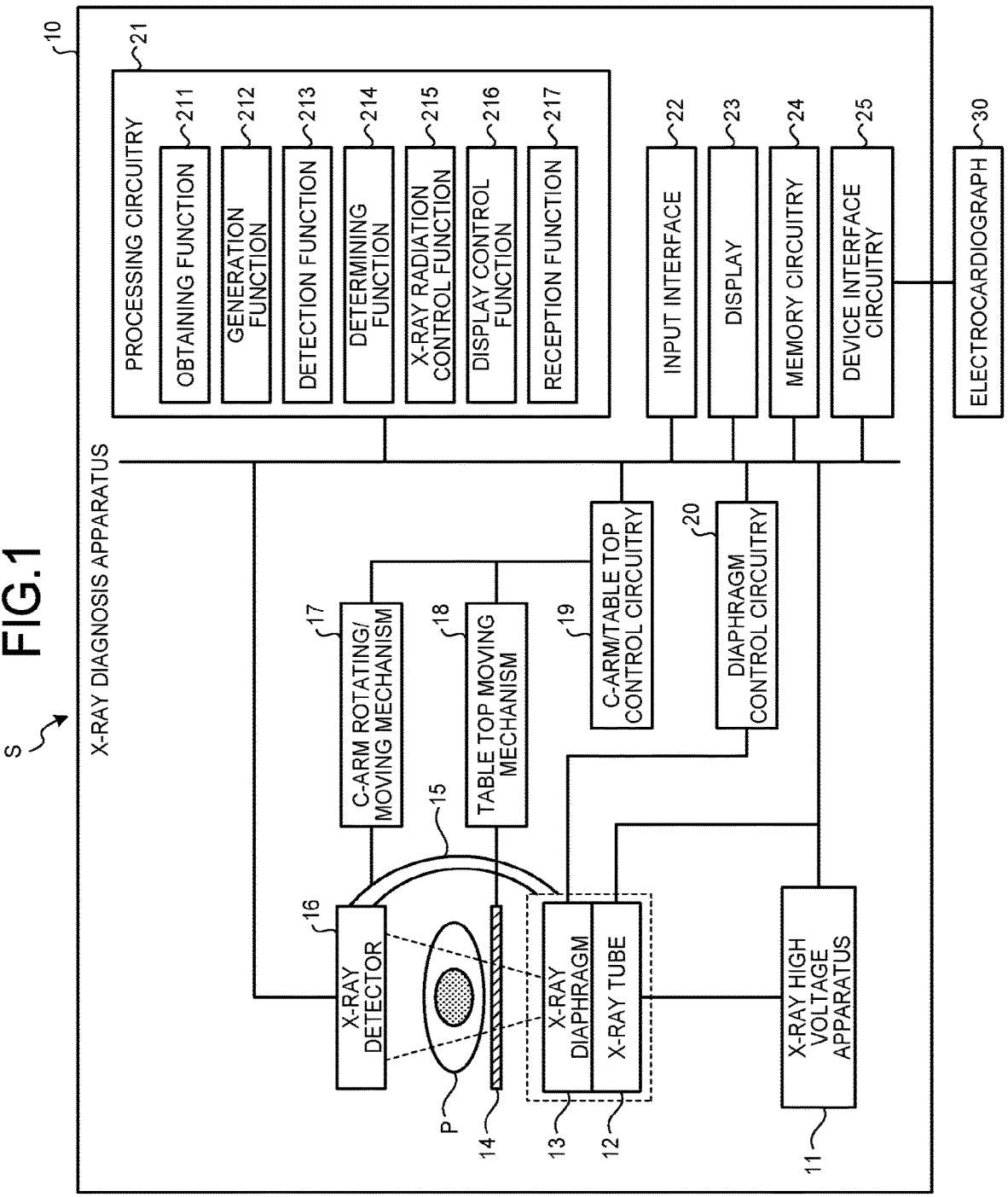
FIG. 1 is a block diagram of an exemplary system structure according to a first embodiment.

FIG. 1 is a block diagram illustrating an exemplary structure of a system S according to a first embodiment. As illustrated in FIG. 1, the system S includes an X-ray diagnosis apparatus 10 and an electrocardiograph 30.

The electrocardiograph 30 functions to obtain electrocardiographic waveform (electrocardiogram: ECG) information about a subject P to transmit the electrocardiogram and time stamp information to the X-ray diagnosis apparatus 10. The time stamp information refers to information representing time at which the electrocardiogram of the subject P is measured.

The X-ray diagnosis apparatus 10 includes an X-ray high voltage apparatus 11, an X-ray tube 12, an X-ray diaphragm 13, a table top 14, a C-arm 15, an X-ray detector 16, a C-arm rotating/moving mechanism 17, a table top moving mechanism 18, a C-arm/table top control circuitry 19, diaphragm control circuitry 20, processing circuitry 21, an input interface 22, a display 23, memory circuitry 24, and device interface circuitry 25. The X-ray diagnosis apparatus 10 may be exemplified by an X-ray angiography apparatus.

The X-ray high voltage apparatus 11 is a high voltage power supply that generates a high voltage to supply the voltage to the X-ray tube 12 under the control of the processing circuitry 21.

The X-ray tube 12 is supplied with a high voltage from the X-ray high voltage apparatus 11 to generate X-rays using the high voltage. The X-ray diaphragm 13 works to converge the X-rays generated by the X-ray tube 12 to selectively irradiate a region of interest (ROI) of the subject P under the control of the diaphragm control circuitry 20.

The table top 14 functions as a bed on which the subject P is to be laid, and is placed on a couch device (not-illustrated). The couch device may be included in the X-ray diagnosis apparatus 10 or provided outside the X-ray diagnosis apparatus 10. The couch device may be included not in the X-ray diagnosis apparatus 10 but in the system S. Needless to say, the subject P is not included in the X-ray diagnosis apparatus 10.

The X-ray detector 16 may be exemplified by an X-ray flat panel detector (FPD) which includes multiple detector elements arrayed in a matrix form. The X-ray detector 16 may be an indirect-conversion detector including a scintillator array and an optical sensor array or a direct-conversion detector including a semiconductor device that converts incident X-rays into electric signals. As an example, the detector elements of the X-ray detector 16 each include a complementary metal oxide semiconductor (CMOS) sensor and a scintillator. The detector elements individually convert and accumulate the detected X-rays into charge and converts the charge into a voltage or a current to generate a detection signal, for example. The X-ray detector 16 outputs the detection signal to the processing circuitry 21.

The C-arm 15 functions to hold the X-ray tube 12, the X-ray diaphragm 13, and the X-ray detector 16. The C-arm rotating/moving mechanism 17 is a mechanism including a motor on a support for rotating and moving the C-arm 15 by driving the motor. The table top moving mechanism 18 is a mechanism for moving the table top 14. For example, the table top moving mechanism 18 includes an actuator and moves the table top 14 using power generated by the actuator.

Under the control of the processing circuitry 21, the C-arm/table top control circuitry 19 functions to control the C-arm rotating/moving mechanism 17 and the table top moving mechanism 18 to regulate the rotation and motion of the C-arm 15 and the motion of the table top 14. The diaphragm control circuitry 20 functions to control the X-ray radiation range with respect to the subject P by regulating the opening of the aperture blade of the X-ray diaphragm 13, under the control of the processing circuitry 21.

The input interface 22 is, for example, implemented by a trackball, a switch button, a mouse, a keyboard, a touch-pad that allows inputs by touching the surface, and a touch-screen being an integration of a display screen and a touch-pad, a non-contact input circuitry including an optical sensor, and audio input circuitry. The input interface 43 is connected to the processing circuitry 21 to convert user inputs into electric signals for output to the processing circuitry 21. The input interface 43 is not limited to the one including a physical operational component such as a mouse or a keyboard. Other examples of the input interface 43 include electrical-signal processing circuitry that receives an electrical signal corresponding to an input from an external input device separated from the apparatus to output the electrical signal to the processing circuitry 21.

The display 23 is, for example, a liquid crystal display (LCD) or an organic electro luminescence display (OELD) and displays various kinds of information. The display 23 displays, for example, a graphical user interface (GUI) that receives various instructions and various kinds of setting from the user via the input interface 22. The display 23 also displays various images generated by the processing circuitry 21. The display 23 is an exemplary display unit. The input interface 22 and the display 23 may form a touch panel.

The device interface circuitry 25 functions to obtain electrocardiogram information and a time stamp from the electrocardiograph 30 for storage in the memory circuitry 24. Alternatively, the device interface circuitry 25 may store the electrocardiogram information in the memory circuitry 24 in association with the time at which the electrocardiogram information is obtained.

The memory circuitry 24 can be implemented by, for example, a semiconductor memory device as a random access memory (RAM) or a flash memory, a hard disk, or an optical disk. As an example, the memory circuitry 24 stores therein programs to be executed by the circuitry included in the X-ray diagnosis apparatus 10.

The processing circuitry 21 is a processor that reads and executes programs from the memory circuitry 24 to implement functions corresponding to the programs. According to an embodiment, the processing circuitry 21 includes an obtaining function 211, a generation function 212, a detection function 213, a determining function 214, an X-ray radiation control function 215, a display control function 216, and a reception function 217. The obtaining function 211 is an exemplary obtainer unit. The generation function 212 is an exemplary generator unit. The detection function 213 is an exemplary detector unit. The determining function 214 is an exemplary determiner unit. The X-ray radiation control function 215 is an exemplary X-ray radiation control unit. The display control function 216 is an exemplary display control unit. The reception function 217 is an exemplary reception unit.

For example, the elements of the processing circuitry 21, i.e., the obtaining function 211, the generation function 212, the detection function 213, the determining function 214, the X-ray radiation control function 215, the display control function 216, and the reception function 217 are individually stored in a computer-executable program format in the memory circuitry 24. The processing circuitry 21 is a processor. For example, the processing circuitry 21 reads and executes programs from the memory circuitry 24 to implement the functions corresponding to the programs. In other words, after loading the respective programs, the processing circuitry 21 includes the respective functions as illustrated in the processing circuitry 21 of FIG. 1. In the example of FIG. 1, the obtaining function 211, the generation function 212, the detection function 213, the determining function 214, the X-ray radiation control function 215, the display control function 216, and the reception function 217 are implemented by the single processor. Instead, the processing circuitry 21 may be constituted of a combination of multiple independent processors so that the individual processors execute the programs to implement the respective functions. In the example of FIG. 1, the programs corresponding to the respective functions are stored in the single piece of memory circuitry 24. Alternatively, multiple memory circuits may be disposed in a distributed manner so that the processing circuitry 21 can read the programs from the individual memory circuits.

In the above description, the processor reads and executes the programs corresponding to the respective functions from the memory circuitry as an example, however, such an example is not to be construed as limiting. The term "processor" used herein signifies, for example, circuitry such as a central processing unit (CPU), a graphical processing unit (GPU), an application specific integrated circuit (ASIC), and a programmable logic device (e.g., a simple programmable logic device (SPLD), a complex programmable logic device (CPLD)), and a field programmable gate array (FPGA). The processor being a CPU, for example, reads and executes the programs from the memory circuitry to implement the functions. In the case of the processor being an ASIC, the programs may be directly embedded as logic circuits in the circuitry of the processor in place of being stored in the memory circuitry 24. In the present embodiment the processors may not be individually configured as a single circuit. Multiple independent circuits may be combined into a single processor to implement the functions. Further, the elements illustrated in FIG. 1 may be integrated into a single processor to implement the functions.

The obtaining function 211 serves to obtain the electrocardiogram information of the subject P from the electrocardiograph 30 via the device interface circuitry 25. The obtaining function 211 also obtains the detection signal detected by the X-ray detector 16. The detection signal is associated with the electrocardiogram information. Specifically, the obtained detection signal and the electrocardiogram become associated with each other through an X-ray radiation time corresponding to the detection signal and a time stamp corresponding to the electrocardiogram information. Alternatively, the obtained detection signal and the electrocardiogram may become associated with each other with reference to an acquisition time of the detection signal, in place of the X-ray radiation time. Further, the association between the electrocardiogram information and the detection signal may be made, for example, based on an elapsed time from an examination start time other than the clock time.

The generation function 212 serves to generate X-ray image data from the detection signal detected by the X-ray detector 16 for storage in the memory circuitry 24. The generation function 212 performs, for example, current/voltage conversion, A/D conversion, and/or parallel/serial conversion to the detection signal detected by the X-ray detector 16 to generate the X-ray image data. The generation function 212 may perform image processing including noise reduction to the X-ray image data. Herein, the X-ray image data is considered to be fluoroscopic X-ray image data by way of example, however, the present embodiment is also applicable to digital angiography (DA) images. The X-ray image data is associated with the electrocardiogram information by clock time, as with the detection signal from which the X-ray image data is generated.

The detection function 213 serves to detect motion of an object or objects rendered in the X-ray image data generated by the generation function 212. The objects or the object rendered in the X-ray image data is an example of an object. The object, which is the object or the objects rendered in the X-ray image data, includes at least one of a device and a part of subject. Objects rendered in the X-ray image data are, for example, devices such as a stent and a catheter. Specifically, the detection function 213 detects device motion rendered in multiple frames of the X-ray image data on a frame basis.

Such a device is manually inserted into a blood vessel of the subject P by a physician. The device may be inserted into the heart or a blood vessel in the vicinity of the heart. In such a case the device may possibly be moved due to the heartbeats even if the physician is not manipulating the device. This may cause a motion blur in the device appearing on the X-ray image data. The magnitude of such device motion may differ depending on the cardiac phase of the heart of the subject P.

Figure 2:
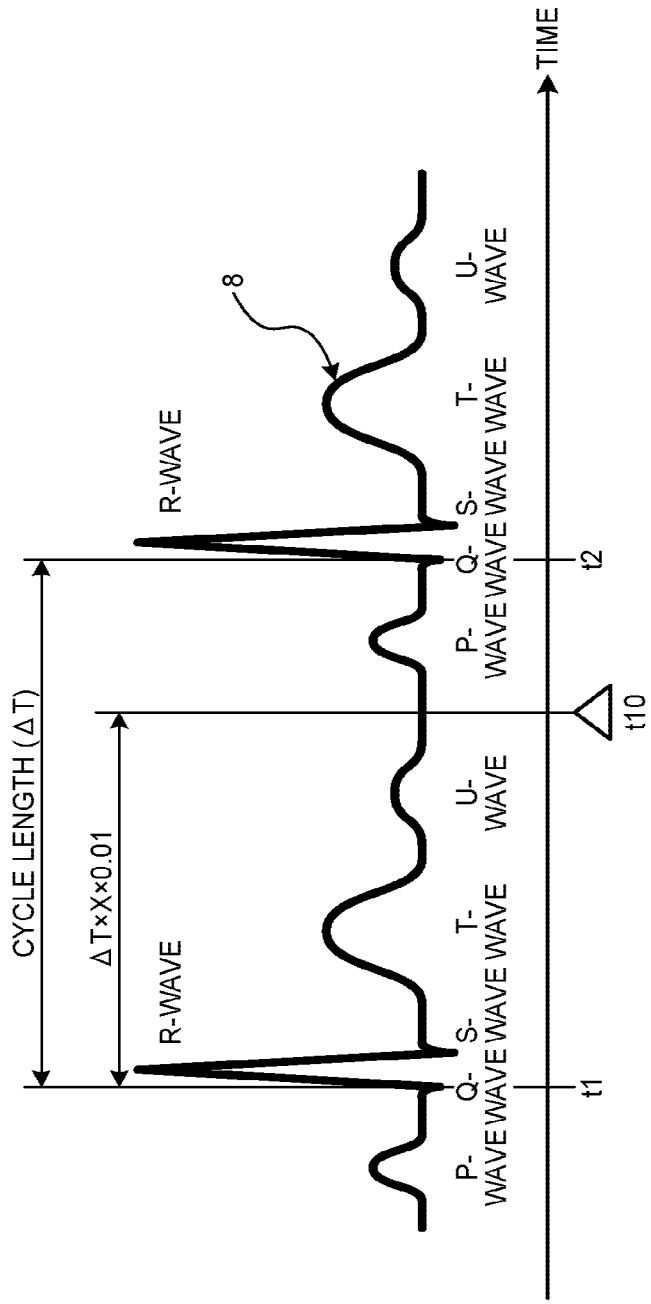
FIG. 2 illustrates an exemplary electrocardiogram according to the first embodiment.

FIG. 2 illustrates an example of an electrocardiographic waveform 8 in the first embodiment. As illustrated in FIG. 2, the electrocardiographic waveform 8 typically includes P-waves, Q-waves, R-waves, S-waves, T-waves, and U-waves. The phases of the electrocardiogram represented by these waves are referred to as cardiac phases. In ECG gated X-ray imaging, a single cycle of the electrocardiogram is identified with reference to the feature points of the electrocardiographic waveform 8. In the example of FIG. 2, the rising of the R-waves is defined as a cycle criterion. Thus, a length of time from time t1 at which the rising of the R-wave is initially measured to time t2 at which the rising of the R-wave is secondly measured is defined as a cycle length.

In the electrocardiographic waveform 8, the magnitude, timing, and cycle length of each wave differ for different subjects P and may differ for different regions of the same subject P. As an example, depending on the tip position of the device to be imaged, e.g., in the vicinity of the left ventricle or the left atrium, the timing at which the device motion due to the heartbeats is decreased differs. The electrocardiographic waveform 8 may also vary depending on the heart rate of the subject P while being imaged.

In the example of FIG. 2, the intermediate cardiac phase between the U-wave and the P-wave is defined as the one in which the device motion due to the heartbeats is decreased in a single cycle, for example. As an example, the X-ray image data with a less motion blur can be obtained by irradiating the subject P with X-rays from the X-ray tube 12 at time t10 in the intermediate phase. Time t10 is a time after X % of the cycle length elapses from time t1. For example, time t10 is expressed by Equation (1):

$$t10 = \Delta T \times X \times 0.01 \text{ where } \Delta T \text{ represents a cycle length.}$$

However, the electrocardiographic waveform 8 differs among different subjects P or different regions of the same subjects P, as described above. Because of this, "X %" defining time t10 also varies among different subjects P or different regions. In this regard the X-ray diagnosis apparatus 10 of the present embodiment determines "X %" defining time t10, based on previously obtained X-ray image data of the subject P and currently obtained electrocardiogram information.

Figure 3:
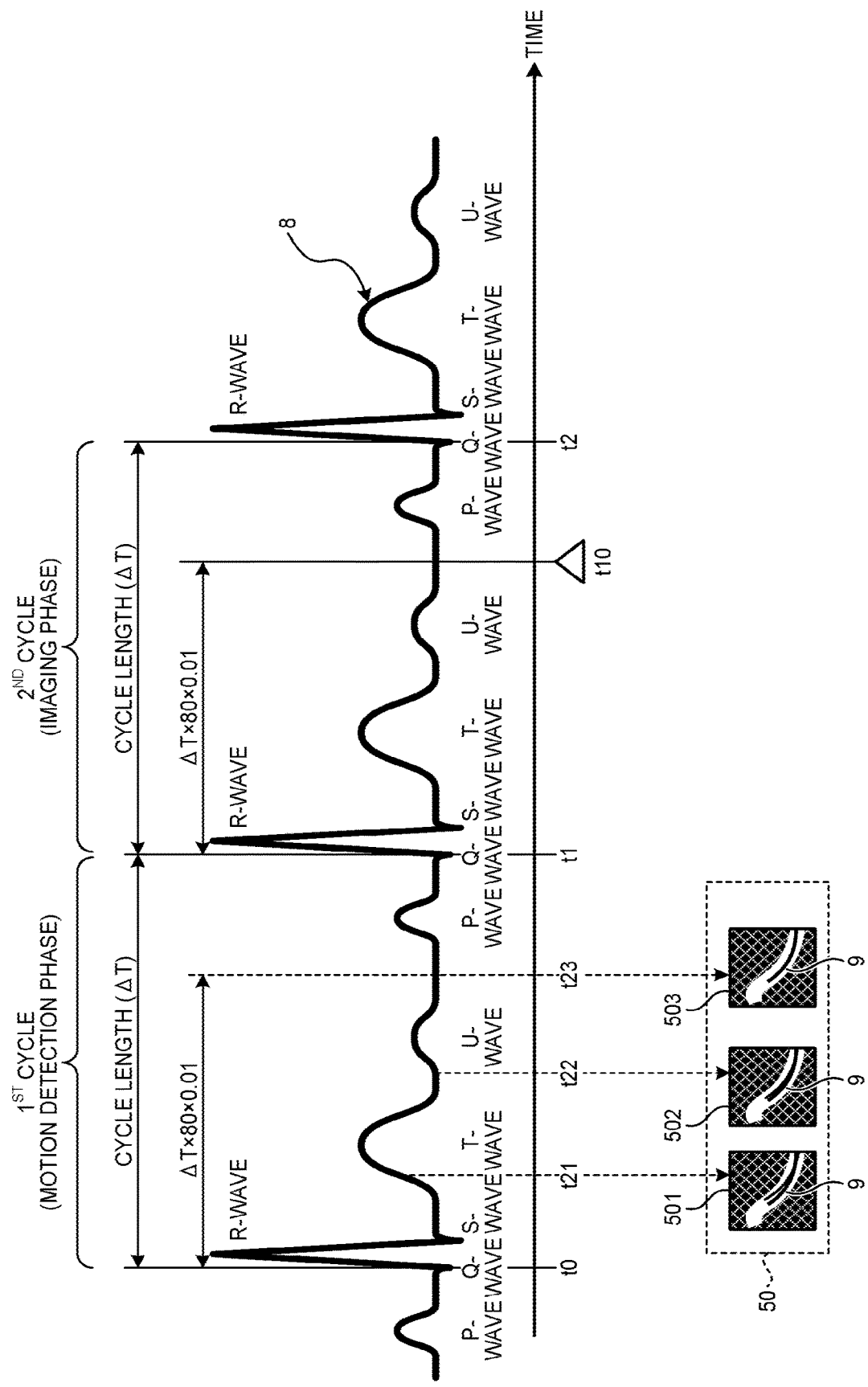
FIG. 3 illustrates an exemplary relationship between X-ray image data 50 and an electrocardiogram.

FIG. 3 illustrates a relationship between the X-ray image data 50 and the electrocardiogram in the first embodiment as an example. In the example of FIG. 3, a motion detection phase as a first cycle is set immediately before an imaging phase as a second cycle. In the motion detection phase the X-ray radiation control function 215 performs imaging of the subject P in a detection/imaging mode, as described later. In the detection/imaging mode, the pulse width of the X-ray radiation is set longer than in the general imaging, to acquire detection signals. The detection/imaging mode will be described in detail below.

In the motion detection phase, the ECG gating is not applied. The X-rays are emitted with predetermined intervals independent from the electrocardiogram. FIG. 3 depicts three X-ray radiation timings in one cycle from time t0 to time t1, however, this is merely exemplary and unintended to limit the number of X-ray radiation timings.

In the example of FIG. 3, the X-ray image data 50 contains frames 501, 502, and 503 generated from the detection signals acquired by continuous X-ray radiation at time t21, t22, t23 in the motion detection phase.

The detection function 213 can detect motion of a device 9 rendered in the frames 501, 502, and 503 of the X-ray image data 50 on a frame basis. In the present embodiment the pulse width of the X-ray radiation is set longer than in the general imaging to acquire the detection signals, so that when the device 9 moves due to the heartbeats, the device 9 may appear to be two or more devices, or the outline of the device 9 may blur in the frames 501, 502, and 503. In other words, the contours of device 9 that are rendered as blurred include those caused by blurring and reduced spatial frequency due to the movement of device 9.

In FIG. 3, for example, the device 9 has moved during the X-ray radiation, therefore, the device 9 appears double in the frames 501 and 502 due to a motion blur. Meanwhile, the device 9 appears to be as it is in the frame 503 because of a minor movement of the device 9 during the X-ray radiation.

By image processing, the detection function 213 detects the magnitude of the motion of the device 9 from the states of the device 9 rendered in the frames 501, 502, and 503. In the example of FIG. 3, the device 9 is most moving in the frame 501, and second most moving in the frame 502, and least moving in the frame 503. The detection function 213 may detect the magnitude of the motion in each of the frames 501 to 503 as numerical values, for example. The numerical values representing the magnitude of the motion detected from each of the frames 501 to 503 are exemplary motion information in the present embodiment. The frames 501 to 503 are associated with the clock time which is associated with the detection signals from which the frames 501 to 503 are generated. Thus, the numerical values representing the magnitude of the motion detected from each of the frames 501 to 503 are associated with the electrocardiographic waveform 8 through the clock time.

Referring back to FIG. 1, the determining function 214 determines an X-ray radiation timing with respect to the subject P, according to the electrocardiographic waveform 8 of the subject P and the motion information in the X-ray image data 50 of the subject P. As described above, the X-ray image data 50 of the subject P is associated with the electrocardiographic waveform 8 of the subject P through, for example, the clock time. Specifically, the determining function 214 determines an X-ray radiation timing according to the magnitude of the motion in each of the frames 501 to 503 of the X-ray image data 50.

For example, the frame 503 exhibits a least amount of motion detected by the detection function 213 among the frames 501, 502, and 503 of the X-ray image data 50 captured in the motion detection phase, as illustrated in FIG. 3.

In this case the determining function 214 determines, as an X-ray radiation timing in the imaging phase, a cardiac phase corresponding to the frame 503 exhibiting the device 9 least moving as detected by the detection function 213 among the frames 501, 502, and 503. The determining function 214 also determines a length of time from start time t0 to end time t1 in the motion detection phase as one cycle length of the electrocardiographic waveform 8 of the subject P.

The cardiac phase corresponding to the frame 503 is determined by an elapsed time from a cycle start, as represented by Equation (1) above. In the example of FIG. 3, a length of time from cycle start time t0 in the motion detection phase to time t23 at which the X-rays are emitted to capture the frame 503 accounts for 80% of the cycle length of the motion detection phase. In this case the determining function 214 determines the value of X defining the X-ray radiation timing in Equation (1) as "80". The determining function 214 regards the cycle length of the imaging phase as the same as the cycle length of the motion detection phase, and determines time t10 after a lapse of 80% of the cycle length from cycle start time t1 in the imaging phase, to be the X-ray radiation timing at which X-ray image data representing the device 9 moving less can be captured. Time t10 after a lapse of 80% of the cycle length is an exemplary first radiation timing in the present embodiment.

FIG. 3 depicts the imaging phase as a single cycle. After time t2, a time after a lapse of 80% of the cycle length from a cycle start time will be the X-ray radiation timing. The cycle lengths of the second and subsequent cycles in the imaging phase can be the same as in the motion detection phase or as that of the immediately previous cycle. Alternatively, the determining function 214 may calculate the cycle length from the heart rate of the subject P at the time when the feature point to be a cycle starting point of the electrocardiographic waveform 8 is measured in the imaging phase.

The value "80" is presented for illustrative purpose only, and the value of X defining the first radiation timing is not limited to 80.

In FIG. 3 the motion detection phase is immediately before the imaging phase. The motion detection phase may be before the imaging phase by two or more cycles.

The X-ray radiation control function 215 serves to repeatedly emit X-rays per cycle of the electrocardiographic waveform 8 of the subject P at the radiation timing determined by the determining function 214.

Specifically, the X-ray radiation control function 215 of the present embodiment includes three imaging modes, i.e., a general imaging mode without ECG gating, a detection/imaging mode, and an ECG gated imaging mode. The imaging modes are selectable by the user, for example.

In the general imaging mode without ECG gating, the X-ray radiation control function 215 causes the X-ray tube 12 to emit X-rays with regular intervals irrespective of the electrocardiographic waveform 8 of the subject P. The general imaging mode including no ECG gating is applied, for example, when the blood vessel to be imaged is far from the heart. In the general imaging mode including no ECG gating, the obtaining function 211 may not obtain the electrocardiogram information.

In the detection/imaging mode, the X-ray radiation control function 215 causes the X-ray tube 12 to emit X-rays at a longer pulse width than in the general imaging mode. For example, the pulse width is set to 6 msec. to 10 msec. in the general imaging mode and the ECG gated imaging mode while the pulse width is set to 12 msec. to 30 msec. two or three times longer than the general pulse width in the detection/imaging mode. As such, setting a longer X-ray pulse width helps render the motion of the device 9 in one frame of X-ray image data 50, as illustrated in FIG. 3. The above-mentioned pulse widths are merely exemplary and not to be construed as limiting. In the detection/imaging mode, the intervals among the X-ray radiation timings are constant independent from the electrocardiographic waveform 8 of the subject P. Further, in the detection/imaging mode the obtaining function 211 obtains the electrocardiogram information for use in determining the radiation timing in the imaging phase, although the X-ray radiation timings are not synchronized with the ECG.

The ECG gated imaging mode is for imaging the subject P after the determining function 214 determines the X-ray radiation timing. In the ECG gated imaging mode, the X-ray radiation control function 215 causes the X-ray tube 12 to emit X-rays to the subject P at the radiation timing determined by the determining function 214 per cycle of the electrocardiographic waveform 8 of the subject P. Alternatively, the ECG gated imaging mode may be automatically started after completion of the detection/imaging mode.

The display control function 216 serves to display a graphical user interface (GUI) and X-ray images on the display 23. For example, the display control function 216 reads the X-ray image data 50 from the memory circuitry 24 for display on the display 23, in response to a user operation via the input interface 22.

The reception function 217 serves to receive user operations via the input interface 22. The reception function 217 receives, for example, a user's selection of one of the imaging modes. The reception function 217 also receives user operations for an imaging start instruction and an imaging end instruction.

Now, a procedure of determining the X-ray radiation timing and the ECG gated imaging to be performed by the X-ray diagnosis apparatus 10 structured as above will be described, as an example.

Figure 4:
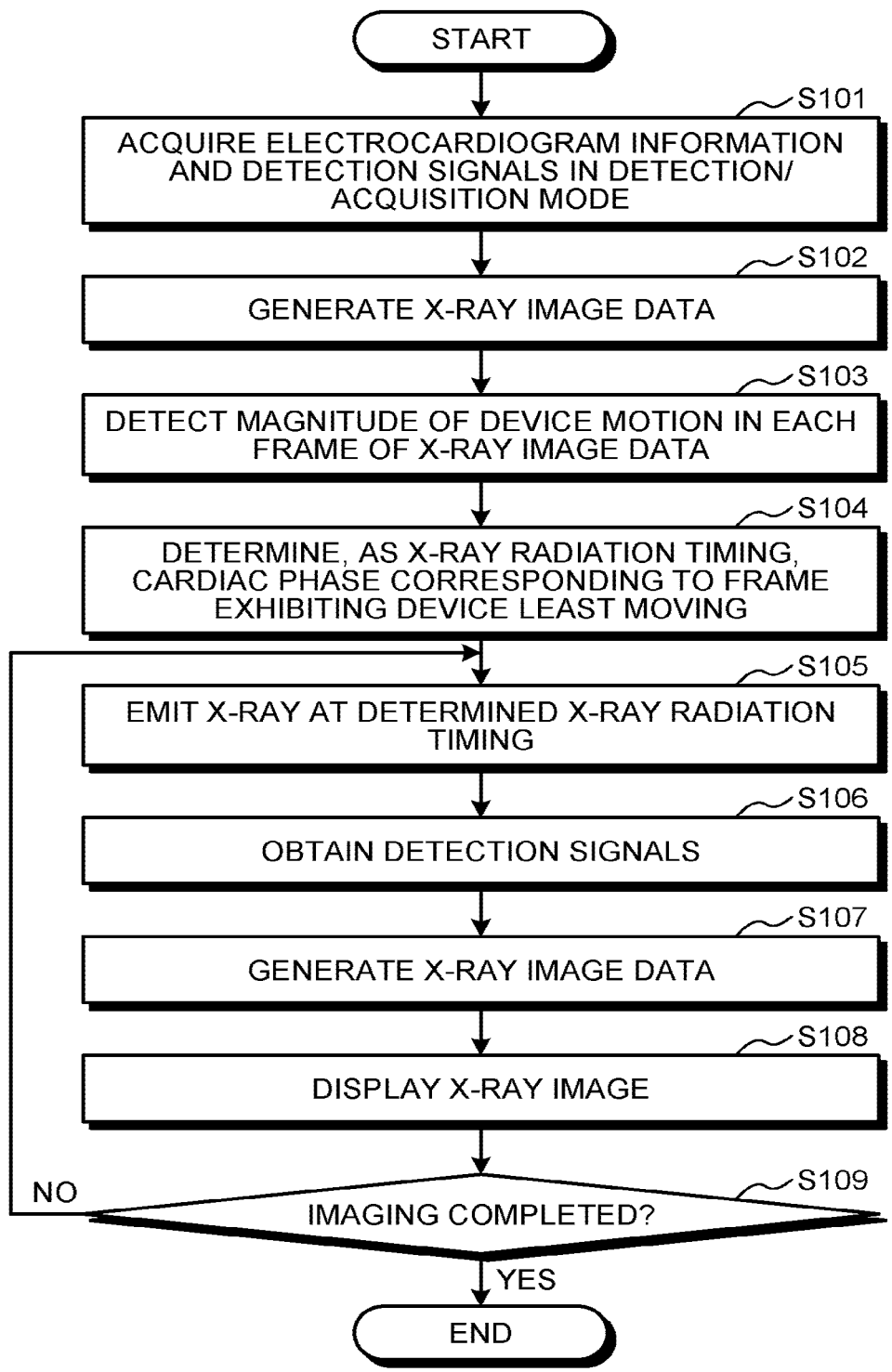
FIG. 4 is a flowchart illustrating an exemplary procedure of determining X-ray radiation timing and ECG gated imaging according to the first embodiment.

FIG. 4 is a flowchart illustrating an exemplary procedure of determining the X-ray radiation timing and the ECG gated imaging according to the first embodiment. In the flowchart, the detection/acquisition mode is assumed to be selected.

The X-ray diagnosis apparatus 10 acquires electrocardiogram information and detection signals in the detection/acquisition mode (S101). Specifically, the X-ray radiation control function 215 causes the X-ray tube 12 to emit X-rays to the subject P at a pulse width twice or three times longer than the general pulse width. The obtaining function 211 obtains the detection signals detected by the X-ray detector 16. The obtaining function 211 also obtains the electrocardiogram information of the subject P from the electrocardiograph 30 via the device interface circuitry 25.

The generation function 212 generates X-ray image data 50 from the detection signals obtained by the obtaining function 211 for storage in the memory circuitry 24 (S102).

The detection function 213 then detects the magnitude of motion of the device 9 in each of the frames 501, 502, and 503 of the X-ray image data 50 (S103).

The determining function 214 determines, as an X-ray radiation timing, a cardiac phase corresponding to the frame exhibiting the device least moving (S104). Specifically, as the X-ray radiation timing in the imaging phase, the determining function 214 determines the cardiac phase corresponding to the frame 503 showing the device least moving among the frames 501, 502, and 503 of the X-ray image data 50 captured in the motion detection phase, as illustrated in FIG. 3.

The ECG gated imaging mode is started, and the X-ray radiation control function 215 causes the X-ray tube 12 to emit X-rays to the subject P at the radiation timing determined by the determining function 214 (S105).

The obtaining function 211 obtains the detection signals detected by the X-ray detector 16 (S106).

The generation function 212 generates X-ray image data 50 from the detection signals obtained by the obtaining function 211 for storage in the memory circuitry 24 (S107).

The display control function 216 then reads the X-ray image data 50 captured in the ECG gated imaging mode from the memory circuitry 24 to display an X-ray image on the display 23 (S108). In addition, the display control function 216 may display an X-ray image based on the X-ray image data 50 captured in the detection/acquisition mode on the display 23.

Unless the reception function 217 receives an imaging end operation from the user (No in S109), the X-ray diagnosis apparatus 10 repeats the processing from S105 to S108.

Upon the reception function 217's receiving the imaging end operation from the user (Yes in S109), the X-ray diagnosis apparatus 10 ends the procedure in the flowchart.

As described above, the X-ray diagnosis apparatus 10 of the present embodiment can determine the first radiation timing for irradiating the subject P with X-rays, on the basis of the information on motion of a object in the X-ray image data 50, the information on motion being calculated by the X-ray image data, the X-ray image data being associated with the electrocardiographic waveform 8 of the subject P, and repeatedly emit X-rays to the subject P at the first radiation timing per cycle of the electrocardiographic waveform 8. Owing to such features, the X-ray diagnosis apparatus 10 of the present embodiment can irradiate the subject P with X-rays at good timing in line with the cardiac phase cycle of the subject P in the ECG gated X-ray imaging.

Herein, "good X-ray radiation timing" refers to X-ray radiation timing at which the X-ray image data 50 with a less motion blur can be obtained, that is, the timing at which the motion of the device 9 due to the heartbeats of the subject P can be decreased. In the present embodiment the X-ray image data 50 includes the frames 501, 502, and 503. The X-ray diagnosis apparatus 10 of the present embodiment can determine the first radiation timing based on the magnitude of motion in each of the frames 501, 502, and 503 of the X-ray image data 50. Thus, the X-ray diagnosis apparatus 10 can accurately determine the X-ray radiation timing at which the X-ray image data 50 with a less motion blur can be obtained.

The X-ray diagnosis apparatus 10 of the present embodiment can detect the motion of the device 9 rendered in each of the frames 501, 502, and 503 of the X-ray image data 50, to determine, as the first radiation timing, the cardiac phase corresponding to the frame exhibiting the device 9 least moving. In the interventional procedure, the physician administers manual procedures to the subject P while capturing an image of the subject P using the X-ray diagnosis apparatus 10. The physician may insert the device 9 into a blood vessel or the heart of the subject P and check the location or position of the device 9 while observing the X-ray image. In such a situation, if the device 9 appears blurry on the X-ray image, the physician may face difficulty in seeing the accurate location or position of the device 9. In this regard the X-ray diagnosis apparatus 10 of the present embodiment can irradiate the subject P with X-rays at the timing when the device 9 is less moved, in synchronization with the electrocardiographic waveform 8 of the subject P. This can help the physicians know the accurate location or position of the device 9.

Second Embodiment

The first embodiment has described an example of setting, as the X-ray radiation timing in the imaging phase, the timing when the X-ray image data 50 with a less motion blur determined in the motion detection phase is obtained. The X-ray diagnosis apparatus 10 emits X-rays at least at such radiation timing, however, it may additionally emit X-rays at different timings.

As in the first embodiment, a system S in the present embodiment includes an X-ray diagnosis apparatus 10 and an electrocardiograph 30. As in the first embodiment, the X-ray diagnosis apparatus 10 in the present embodiment includes an X-ray high voltage apparatus 11, an X-ray tube 12, an X-ray diaphragm 13, a table top 14, a C-arm 15, an X-ray detector 16, a C-arm rotating/moving mechanism 17, a table top moving mechanism 18, a C-arm/table top control circuitry 19, diaphragm control circuitry 20, processing circuitry 21, an input interface 22, a display 23, memory circuitry 24, and device interface circuitry 25.

As in the first embodiment, the processing circuitry 21 in the X-ray diagnosis apparatus 10 includes an obtaining function 211, a generation function 212, a detection function 213, a determining function 214, an X-ray radiation control function 215, a display control function 216, and a reception function 217.

The obtaining function 211, the generation function 212, the detection function 213, the X-ray radiation control function 215, the display control function 216, and the reception function 217 include similar or same functions as those in the first embodiment.

In the present embodiment, the determining function 214 determines a predetermined number of X-ray radiation timings per cycle of the electrocardiographic waveform 8 of the subject P, in addition to the X-ray radiation timing in the first embodiment.

Figure 5:
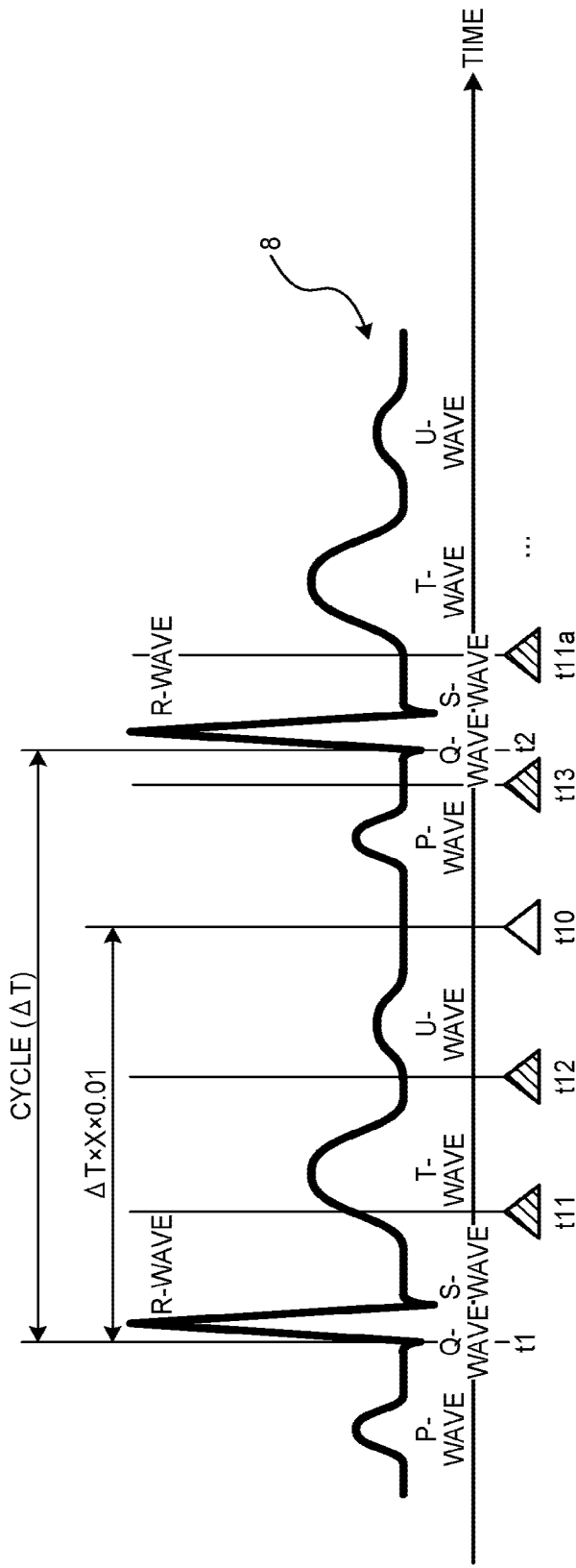
FIG. 5 illustrates an exemplary X-ray radiation timing according to a second embodiment.

FIG. 5 illustrates X-ray radiation timings according to the second embodiment by way of example. In the example of FIG. 5, the determining function 214 determines four X-ray radiation timings including time t10 per cycle of the electrocardiographic waveform 8 of the subject P. The number is merely exemplary and the number of times at which X-rays are emitted per cycle is not limited to four.

Time t10 is a first X-ray radiation timing corresponding to the frame 503 exhibiting the device 9 least moving among the frames of the X-ray image data 50 detected in the motion detection phase, as in the first embodiment.

In addition to the first X-ray radiation timing, the determining function 214 of the present embodiment determines a predetermined number of X-ray radiation timings per cycle of the electrocardiographic waveform 8 of the subject P. Specifically, the determining function 214 may determine additional X-ray radiation timings, i.e., times t11, t12, and t13 by equally dividing the interval including time t10 from time t1 to time t2, that is, a cycle length. The intervals between the radiation timings may not be completely constant. Times t11, t12, and t13 defining the radiation timings may be set such that differences in the intervals between time t1 and time t11, between time t11 and time t12, between time t12 and time t10, between time t12 and time t10, and between time t10 and time t13 are equal to or below a threshold.

Further, the determining function 214 determines three radiation timings corresponding to times t11, t12, and t13 per cycle of the electrocardiographic waveform 8 of the subject P. For example, time t11a shown in FIG. 5 is determined as a radiation timing in the same manner as time t11 in the immediately previous cycle. The determining function 214 uses the length of the immediately previous cycle to calculate the radiation timing. For example, the determining function 214 uses the interval between time t1 and time t2 to calculate a radiation timing in the cycle starting from time t2. Alternatively, the determining function 214 may calculate the cycle length from the heart rate of the subject P at the time when a feature point as a cycle starting point of the electrocardiographic waveform 8 is measured in the imaging phase.

As such, the X-ray diagnosis apparatus 10 of the present embodiment determines a predetermined number of X-ray radiation timings per cycle of the electrocardiographic waveform 8 of the subject P, in addition to the first X-ray radiation timing. Thereby, the X-ray diagnosis apparatus 10 of the present embodiment can allow the physician to see the state of a region of interest in real time, by more frequently capturing the image of the subject P other than the timing at which a motion blur of the device 9 is decreased, in addition to exerting the effects of the first embodiment.

Third Embodiment

The second embodiment has described determining multiple radiation timings by dividing the cycle length of the electrocardiographic waveform 8 by a predetermined number, as an example. In a third embodiment, multiple radiation timings are determined by varying the value of "X" defining the radiation timing.

Figure 6:
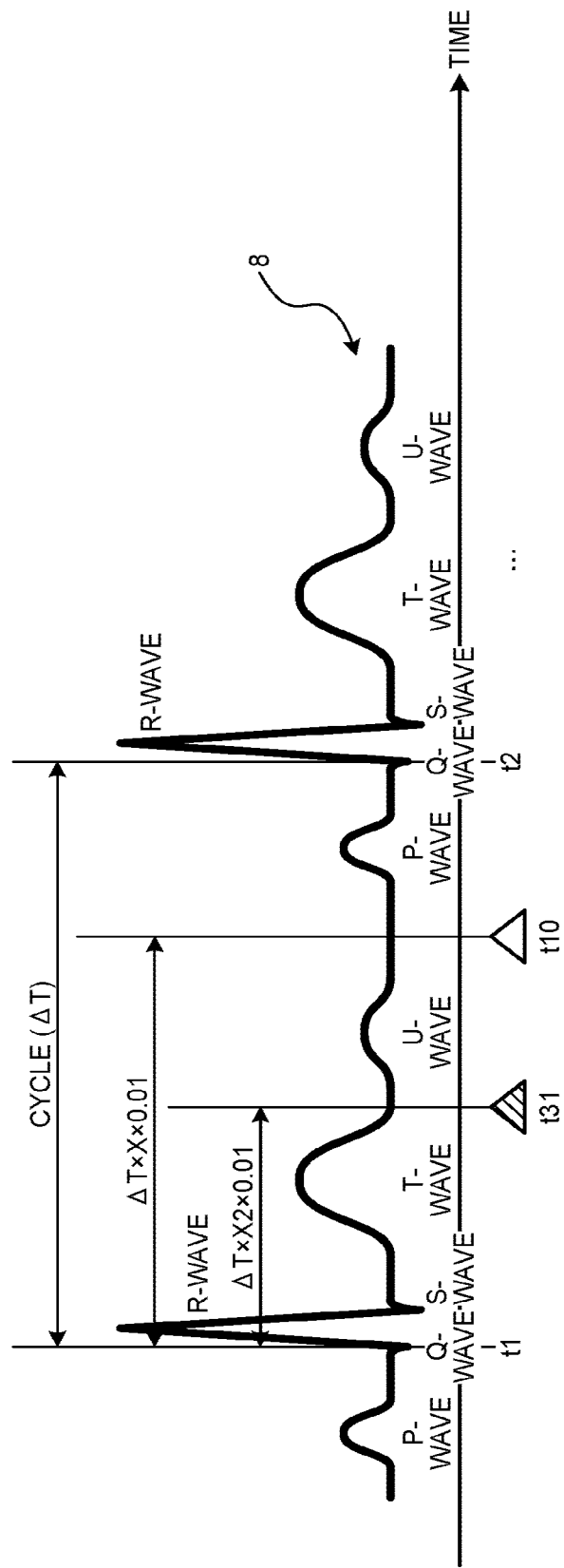
FIG. 6 illustrates an exemplary X-ray radiation timing according to a third embodiment.

FIG. 6 illustrates exemplary X-ray radiation timings according to the third embodiment. As illustrated in FIG. 6, the determining function 214 determines, as X-ray radiation timings, time t10 after a lapse of X % of the cycle length from time t1 and time t31 after a lapse of X2% of the cycle length from time t1.

Time t10 is the first radiation timing corresponding to the frame 503 exhibiting the device 9 least moving among the frames of the X-ray image data 50 detected in the motion detection phase, as in the first embodiment.

The value of X2 defining time t31 is not limited to a particular value and may be designated by the user or may be preset. Further, the number of other radiation timings in addition to the first radiation timing is not limited to one. Different percentages defining different timings may be set.

Fourth Embodiment

According to any of the first to third embodiments, the X-ray diagnosis apparatus 10 automatically determines the radiation timing and emit X-rays at the determined radiation timing, as an example. In a fourth embodiment the user is allowed to set the X-ray radiation timing.

As in the first embodiment, a system S in the present embodiment includes an X-ray diagnosis apparatus 10 and an electrocardiograph 30. As in the first embodiment, the X-ray diagnosis apparatus 10 in the present embodiment includes an X-ray high voltage apparatus 11, an X-ray tube 12, an X-ray diaphragm 13, a table top 14, a C-arm 15, an X-ray detector 16, a C-arm rotating/moving mechanism 17, a table top moving mechanism 18, a C-arm/table top control circuitry 19, diaphragm control circuitry 20, processing circuitry 21, an input interface 22, a display 23, memory circuitry 24, and device interface circuitry 25.

As in the first embodiment, the processing circuitry 21 in the X-ray diagnosis apparatus 10 includes an obtaining function 211, a generation function 212, a detection function 213, a determining function 214, an X-ray radiation control function 215, a display control function 216, and a reception function 217.

The obtaining function 211, the generation function 212, the detection function 213, and the determining function 214 include similar or same functions as those in the first embodiment.

Figure 7:
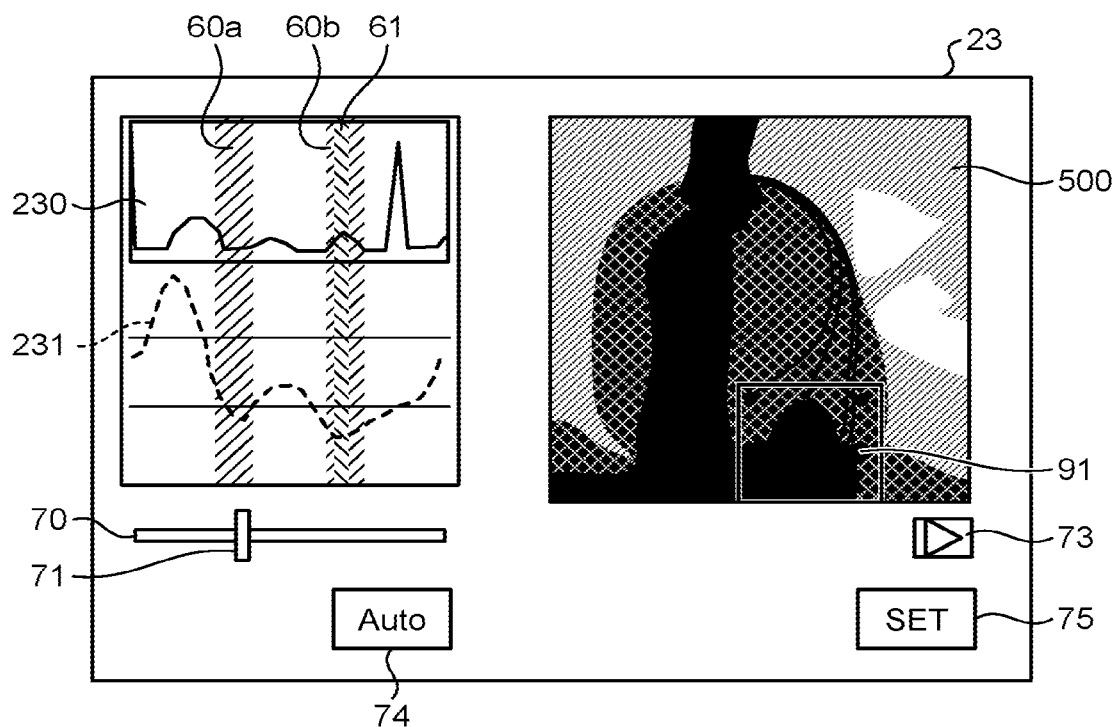
FIG. 7 illustrates an exemplary setting screen for X-ray radiation timing according to a fourth embodiment.

FIG. 7 illustrates an X-ray radiation timing setting screen according to the fourth embodiment by way of example. As illustrated in FIG. 7, the display control function 216 of the present embodiment displays a graph 231, an electrocardiogram 230 representing the electrocardiographic waveform 8 of the subject P, and a slider bar 70 with a tub 71 on the display 23, in association with one another. The graph 231 represents the magnitude of motion in each of the frames of the X-ray image data 50. The slider bar 70 and the tub 71 allow the user to designate the radiation timing.

The graph 231 graphically depicts numerical values indicating the magnitude of motion in each of the frames detected by the detection function 213 in the motion detection phase. The graph 231 representing the magnitude of motion in each of the frames and the electrocardiogram 230 representing the electrocardiographic waveform 8 of the subject P in the motion detection phase are displayed together in the same timeline.

A vertical line 61 is displayed on the graph 231 and the electrocardiogram 230, representing the first X-ray radiation timing determined by the determining function 214. Vertical lines 60a and 60b represent end-systolic and mid-diastolic phases of the electrocardiographic waveform 8 of the subject P, respectively. The display of the vertical lines 60a, 60b, and 61 may not be essential.

The slider bar 70 and the tub 71 are an exemplary operative element on the screen. The horizontal axis of the slider bar 70 indicates time in the graph 231 and the electrocardiogram 230. By moving the tub 71 on the setting screen, the user can at least either change the first radiation timing or add another radiation timing. For example, the user may be able to designate an additional radiation timing using the tub 71 while maintaining the first radiation timing. Alternatively, the user may be able to change the first radiation timing by manipulating the tub 71. In the present embodiment, changing the first radiation timing and adding another radiation timing are collectively referred to an X-ray radiation timing designation by the user.

In the example of FIG. 7, the display control function 216 displays, on the setting screen, an X-ray image 500 based on the X-ray image data 50 captured in the motion detection phase. The X-ray image 500 is an image of a frame corresponding to the detection signal of the X-ray emitted at the time indicated by the tub 71, among the frames included in the X-ray image data 50 captured in the motion detection phase.

In response to the user's moving the tub 71, the display control function 216 displays the X-ray image 500 of the frame corresponding to the detection signal of the X-ray emitted at the time indicated by the tub 71 after moved. Such a display allows the user to designate the radiation timing by moving the tub 71 at the time when the device 9 rendered has a less motion blur on the X-ray image 500.

Referring to FIG. 7, the display control function 216 displays both the graph 231 representing the magnitude of the motion in each of the frames and the X-ray image 500 based on the X-ray image data 50 captured in the motion detection phase. However, the display control function 216 may display only either of the graph 231 and the X-ray image 500.

The setting screen further includes a reproduce/stop button 73, an Auto button 74, and a set button 75.

The reproduce/stop button 73 is an operation button which allows the user to select a continuous display of the X-ray image 500 being the frames of the X-ray image data 50 captured in the motion detection phase. Specifically, upon a user's press onto the reproduce/stop button 73, the frames of the X-ray image data 50 are reproduced frame by frame.

The user may press the reproduce/stop button 73 during the continuous display of the frames of the X-ray image 500. Thereby, the X-ray image 500 being currently on display freezes as it is. While the different frames of the X-ray image 500 are being displayed one after another by the reproduce/stop button 73 being pressed, the tub 71 moves along the slider bar 70 in accordance with the frame being displayed. When the continuous display of the different frames of the X-ray image 500 stops by the reproduce/stop button 73 being pressed, the tub 71 also stops moving. Thus, the user may designate the X-ray radiation timing by pressing the reproduce/stop button 73 at the timing when his or her desired X-ray image 500 appears on the screen, in place of manipulating the tub 71.

The Auto button 74 is an operation button that allows the user to return the X-ray radiation timing to the first radiation timing automatically determined by the determining function 214.

The set button 75 is an operation button that allows the user to set the X-ray radiation timing.

The reception function 217 receives the X-ray radiation timing as designated by the user through the manipulation of the operative element on display, in addition to including similar or same functions according to the first embodiment. Specifically, the reception function 217 receives at least either of a change of the first radiation timing through the manipulation of the operative element and an addition of another radiation timing made by the user. For example, the reception function 217 receives a user operation to move the tub 71. The reception function 217 receives a user operation to press the reproduce/stop button 73, the Auto button 74, and the set button 75.

In response to the user operation to add or change the X-ray radiation timing on the setting screen, the X-ray radiation control function 215 causes the X-ray tube 12 to emit X-rays in the ECG gated imaging mode at the X-ray radiation timing added or after the change, in addition to including similar or same functions according to the first embodiment.

As such, the X-ray diagnosis apparatus 10 of the present embodiment displays, on the display 23, the graph 231 representing the magnitude of motion in each of the frames of the X-ray image data 50 of the subject P, the electrocardiographic waveform 8 of the subject P, and the slider bar 70 with the tub 71 that allow the user to designate the X-ray radiation timing with respect to the subject P, in association with one another. The X-ray diagnosis apparatus 10 then receives the radiation timing as designated by the user through the manipulation of the tub 71. In this manner the X-ray diagnosis apparatus 10 of the present embodiment can allow the user to designate his or her desired X-ray radiation timing at which a motion blur due to the heartbeats of the subject P on the image is decreased, in addition to exerting similar or same effects as in the first embodiment.

Fifth Embodiment

In the fourth embodiment the user is allowed to set one radiation timing. Alternatively, the user may be allowed to set any number of radiation timings.

Figure 8:
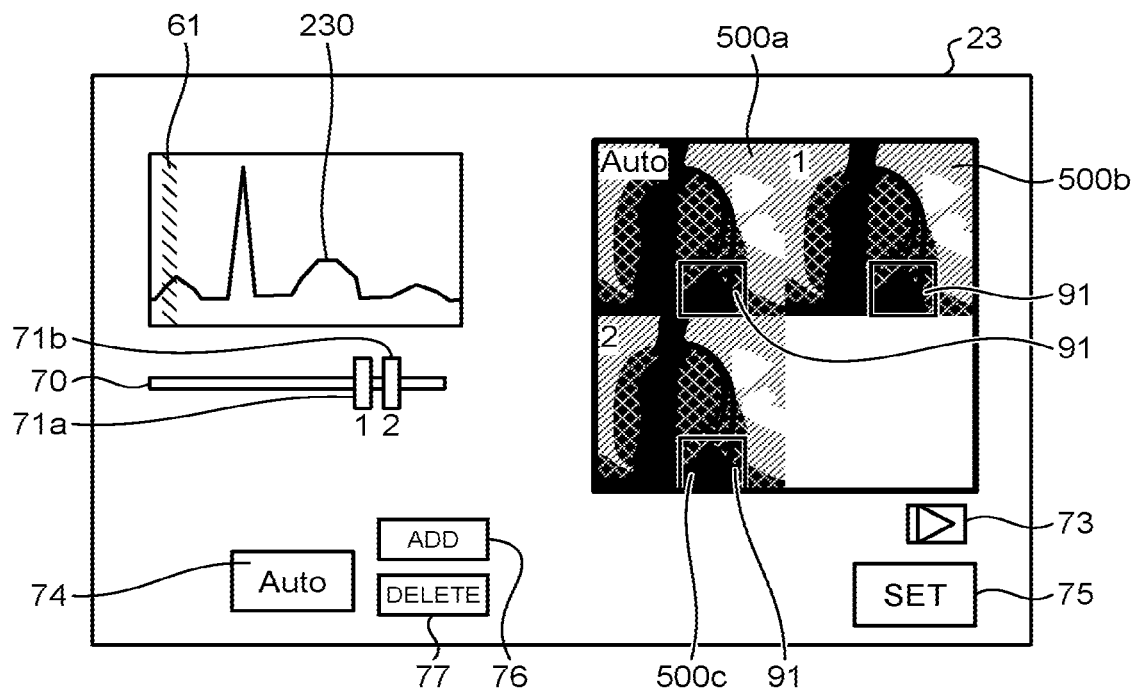
FIG. 8 illustrates an exemplary setting screen for X-ray radiation timing according to a fifth embodiment.

FIG. 8 illustrates an exemplary X-ray radiation timing setting screen according to a fifth embodiment. As in the fourth embodiment, the display control function 216 displays the setting screen on the display 23.

In the present embodiment the setting screen includes an add button 76 and a delete button 77.

The add button 76 is an operation button that allows the user to add a tub 71 on the slider bar 70. In the example of FIG. 8, a first tub 71a and a second tub 71b are displayed. In the initial state, for example, only the first tub 71a is displayed. By a user's pressing the add button 76, the second tub 71b is additionally displayed. The user may further press the add button 76 to display three or more tubs 71.

The delete button 77 is an operation button that allows the user to delete the tub or tubs 71 on the slider bar 70. For example, upon one user's press to the delete button 77, one tub 71 on the slider bar 70 is deleted. In the case of only one tub 71 displayed on the display, the tub 71 cannot be deleted even if the user presses the delete button 77.

The user can thus set any number of radiation timings by manipulating the add button 76 and the delete button 77.

The display control function 216 of the present embodiment displays, on the setting screen, multiple X-ray images based on the frames of the X-ray image data 50 of the subject P captured in the motion detection phase, and the electrocardiogram 230 representing the electrocardiographic waveform 8 of the subject P in association with each other.

FIG. 8 depicts a display of an Auto image 500a, a first image 500b, and a second image 500c, as an example.

The Auto image 500a is an X-ray image of a frame corresponding to the first X-ray radiation timing determined by the determining function 214, among the frames of the X-ray image data 50. The Auto image 500a corresponds to the vertical line 61, displayed on the electrocardiogram 230, representing the first X-ray radiation timing determined by the determining function 214.

The first image 500b is an X-ray image of a frame corresponding to the detection signal of the X-ray emitted at the time indicated by the first tub 71a, among the frames of the X-ray image data 50.

The second image 500c is an X-ray image of a frame corresponding to the detection signal of the X-ray emitted at the time indicated by the second tub 71b, among the frames of the X-ray image data 50.

As the number of the tubs 71 increases, the number of the X-ray images displayed on the setting screen increases. The user may press the reproduce/stop button 73 while a display area showing any of the X-ray images on the setting screen is being selected. This changes the frames to be displayed from one to another in chronological order starting from the X-ray image of the frame currently on display, to reproduce and display the consecutive frames of the X-ray image on the display area. In this case the tub 71 corresponding to the display area also changes in position.

The Auto button 74 and the set button 75 have similar or same functions as in the fourth embodiment.

As illustrated in FIG. 7, the display control function 216 may display the vertical lines 60a and 60b representing end-systolic and mid-diastolic phases of the electrocardiographic waveform 8 of the subject P. In FIG. 8 the graph 231 representing the magnitude of motion in each of the frames may also be displayed, as in FIG. 7.

In addition to including similar or same functions as in the first embodiment, the reception function 217 receives a designation of an X-ray radiation timing with respect to the subject P made by the user with reference to the electrocardiogram 230 representing the electrocardiographic waveform 8. For example, the user may move the tub 71 displayed below the electrocardiogram 23 representing the electrocardiographic waveform 8 to change the first radiation timing, or may press the add button 76 to add another radiation timing. The reception function 217 receives at least either of the user operations.

As such, the X-ray diagnosis apparatus 10 of the present embodiment displays, on the display 23, the X-ray images 500*a*, 500*b*, and 500*c* based on the frames of the X-ray image data 50 of the subject P and the electrocardiographic waveform 8 of the subject P in association with each other. The X-ray diagnosis apparatus 10 then receives a designation of the X-ray radiation timing with respect to the subject P made by the user referring to the electrocardiographic waveform 8. In this manner the X-ray diagnosis apparatus 10 of the present embodiment can allow the user to designate two or more desirable X-ray radiation timings while visually checking the state of a motion blur appearing on the X-ray images 500*a*, 500*b*, and 500*c*, in addition to exerting similar or same effects as in the first embodiment.

Sixth Embodiment

In a sixth embodiment the X-ray diagnosis apparatus 10 adjusts the X-ray radiation timing in accordance with the characteristics of the X-ray detector 16, as an example.

As in the first embodiment, a system S in the present embodiment includes an X-ray diagnosis apparatus 10 and an electrocardiograph 30. As in the first embodiment, the X-ray diagnosis apparatus 10 in the present embodiment includes an X-ray high voltage apparatus 11, an X-ray tube 12, an X-ray diaphragm 13, a table top 14, a C-arm 15, an X-ray detector 16, a C-arm rotating/moving mechanism 17, a table top moving mechanism 18, a C-arm/table top control circuitry 19, diaphragm control circuitry 20, processing circuitry 21, an input interface 22, a display 23, memory circuitry 24, and device interface circuitry 25.

In the present embodiment, for example, the X-ray detector 16 of the X-ray diagnosis apparatus 10 may accumulate and read electric charge in a regular cycle.

As in the first embodiment, the processing circuitry 21 of the X-ray diagnosis apparatus 10 includes an obtaining function 211, a generation function 212, a detection function 213, a determining function 214, an X-ray radiation control function 215, a display control function 216, and a reception function 217.

The obtaining function 211, the generation function 212, the detection function 213, the X-ray radiation control function 215, the display control function 216, and the reception function 217 include similar or same functions as those in the first embodiment.

Figure 9:
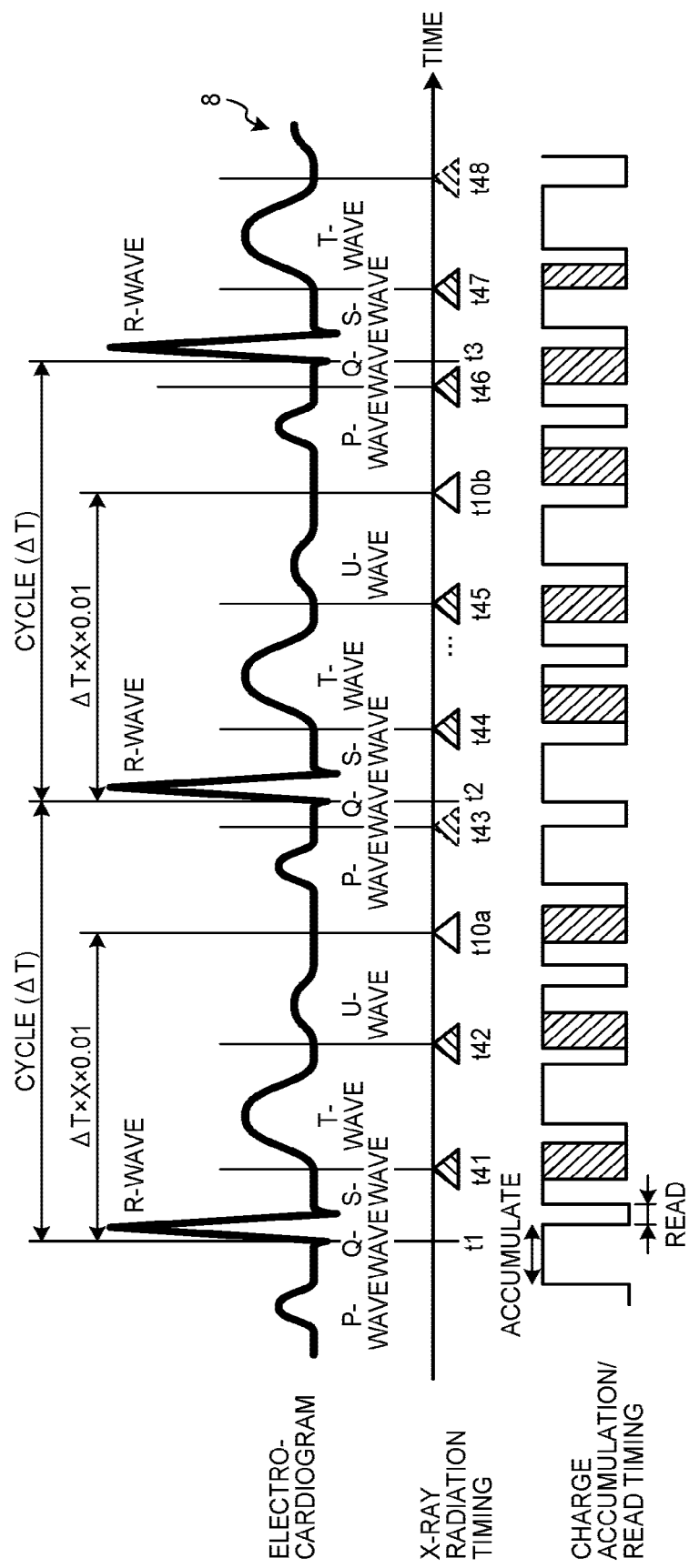
FIG. 9 illustrates an electrocardiogram, X-ray radiation timing, and charge accumulation/read timing of an X-ray detector, by way of example.

FIG. 9 illustrates an electrocardiographic waveform 8, X-ray radiation timing, and charge accumulation/read timing by the X-ray detector 16 in the sixth embodiment by way of example. As illustrated in FIG. 9, the X-ray detector 16 accumulates and reads electric charge in a regular cycle.

The X-ray detector 16 detects X-rays emitted during a charge accumulation period while detecting no X-rays emitted during a charge read period.

In the present embodiment the determining function 214 adjusts the radiation timing in line with the charge accumulation period of the X-ray detector 16. The adjustment method includes, for example, decreasing the number of radiation timings or shifting the radiation timing.

In the present embodiment, multiple X-ray radiation timings are set per cycle of electrocardiographic waveform 8 of the subject P as illustrated in FIG. 9. The radiation timings except for the first radiation timing can be set by, for example, any of the setting methods described in the second to sixth embodiments.

In the example of FIG. 9, time t10a and time t10b correspond to the first radiation timing.

When the radiation timing is included in the charge accumulation period of the X-ray detector 16, the determining function 214 uses the radiation timing without adjusting it. In the example of FIG. 9, times t10a, t41, t42, t44, t45, t10b, t46, and t47 are radiation timings in the charge accumulation period.

When the radiation timing is included not in the charge accumulation period but in the charge read period of the X-ray detector 16, the determining function 214 adjusts the radiation timing. In the example of FIG. 9, times t43 and t48 are radiation timings in the charge read period. In FIG. 9 the determining function 214 excludes time t43 and time t48 from the X-ray radiation timings. In other words, the determining function 214 decreases the number of radiation timings.

In FIG. 9 time t43 and time t48 are to be adjusted, however, they are merely exemplary and not to be construed as limiting. For example, time t10a and time t10b corresponding to the first radiation timing may be adjusted.

As such, the X-ray diagnosis apparatus 10 of the present embodiment adjusts the first radiation timing or other radiation timings in line with the charge accumulation period of the X-ray detector. Because of this, the X-ray diagnosis apparatus 10 of the present embodiment can emit X-rays at good timing depending on the characteristics of the X-ray detector 16, in addition to exerting similar or same effects as that of the first embodiment.

Although in the present embodiment the first radiation timing is adjustable as with other radiation timings, the determining function 214 may exclude the first radiation timing from the timings to be adjusted.

Seventh Embodiment

The first embodiment has described an example that device motion rendered in the frames of the X-ray image data 50 is detected on a frame basis. In a seventh embodiment, a change in position of the device rendered in two chronologically adjacent frames is detected, as an example.

As in the first embodiment, a system S in the present embodiment includes an X-ray diagnosis apparatus 10 and an electrocardiograph 30. As in the first embodiment, the X-ray diagnosis apparatus 10 in the present embodiment includes an X-ray high voltage apparatus 11, an X-ray tube 12, an X-ray diaphragm 13, a table top 14, a C-arm 15, an X-ray detector 16, a C-arm rotating/moving mechanism 17, a table top moving mechanism 18, a C-arm/table top control circuitry 19, diaphragm control circuitry 20, processing circuitry 21, an input interface 22, a display 23, memory circuitry 24, and device interface circuitry 25.

As in the first embodiment, the processing circuitry 21 of the X-ray diagnosis apparatus 10 includes an obtaining function 211, a generation function 212, a detection function 213, a determining function 214, an X-ray radiation control function 215, a display control function 216, and a reception function 217.

The obtaining function 211, the generation function 212, the display control function 216, and the reception function 217 include similar or same functions as those in the first embodiment.

Figure 10:
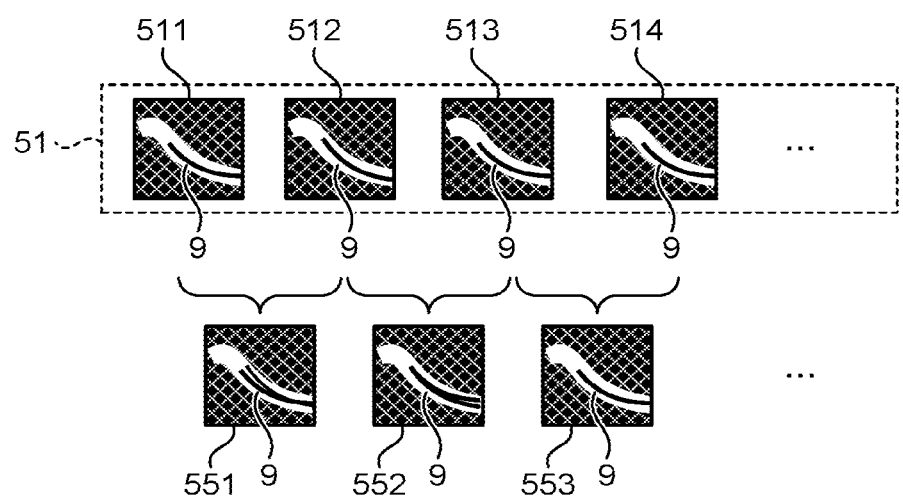
FIG. 10 illustrates an example of detecting the magnitude of device motion in multiple frames included in X-ray image data according to a seventh embodiment.

FIG. 10 illustrates an exemplary detection method of the magnitude of motion of the device 9 in frames 511, 512, 513, and 514 of X-ray image data 51. The number of frames in FIG. 10 is merely exemplary and not to be construed as limiting.

The frames 511, 512, 513, and 514 base on the detection signals of X-rays emitted in a time series in the motion detection phase. The frames 511, 512, 513, and 514 are captured in the detection/imaging mode.

In the present embodiment, the detection signals are acquired at a higher rate in the detection/imaging mode than in the general imaging mode. Thus, an imaging time per frame is shortened so that it is difficult to detect motion of the device 9 from one frame. In addition, the detection/imaging mode of the present embodiment does not involve ECG gating, and the X-ray radiation timing is set at regular intervals independent from the electrocardiographic waveform 8 of the subject P. In the detection/imaging mode, however, the obtaining function 211 obtains the electrocardiogram information for use in determining the radiation timing in the imaging phase, as in the first embodiment.

The detection function 213 of the present embodiment adds two chronologically adjacent frames among the frames 511, 512, 513, and 514 of the X-ray image data 51. Specifically, the detection function 213 adds, for example, the frames 511 and 512. The two added frames are defined as an added frame 551. The devices 9 rendered in the two frames 511, 512 are combined in one added frame 551.

The detection function 213 also adds the frame 512 and the frame 513 as well as the frame 513 and the frame 514 to generate an added frame 552 and an added frame 553, respectively.

The detection function 213 detects a change in position of the device rendered in each two chronologically adjacent frames from the added frames 551, 552, 553. For example, a difference in position of the device 9 appearing in the two frames 511, 512 may cause a motion blur and the device 9 may appear double in the added frame 551. The detection function 213 detects the magnitude of the motion of the device 9 appearing in the added frame 551, 552, 553 through image processing.

In the example of FIG. 10, the device 9 is most moving in the added frame 55, second most moving in added frame 552, and least moving in the added frame 553. In this case, the device 9 moves less in a period from X-ray radiation for capturing the frame 513 to X-ray radiation for capturing the frame 514 than in periods between pieces of X-ray radiation for capturing the other frames. The magnitude of the motion detected by the detection function 213 may be represented in, for example, numerical values.

In the present embodiment the determining function 214 determines, as the first radiation timing, a cardiac phase corresponding to the added frame 553 exhibiting the device 9 least changing in position as detected by the detection function 213, in addition to including similar or same functions as in the first embodiment.

The cardiac phase corresponding to the added frame 553 exhibiting the device 9 least changing in position is, for example, an X-ray radiation timing for the preceding frame 513 between the two frames 513 and 514 on which the added frame 553 bases. In the example of FIG. 10, the determining function 214 determines the X-ray radiation timing with respect to the frame 513 as the first radiation timing.

In the present embodiment the X-ray radiation control function 215 acquires the detection signals for imaging at a higher rate in the detection/imaging mode than in the general imaging mode, in addition to including similar or same functions as in the first embodiment. The general imaging mode without ECG gating and the ECG gated imaging mode are similar or same as in the first embodiment.

Figure 11:
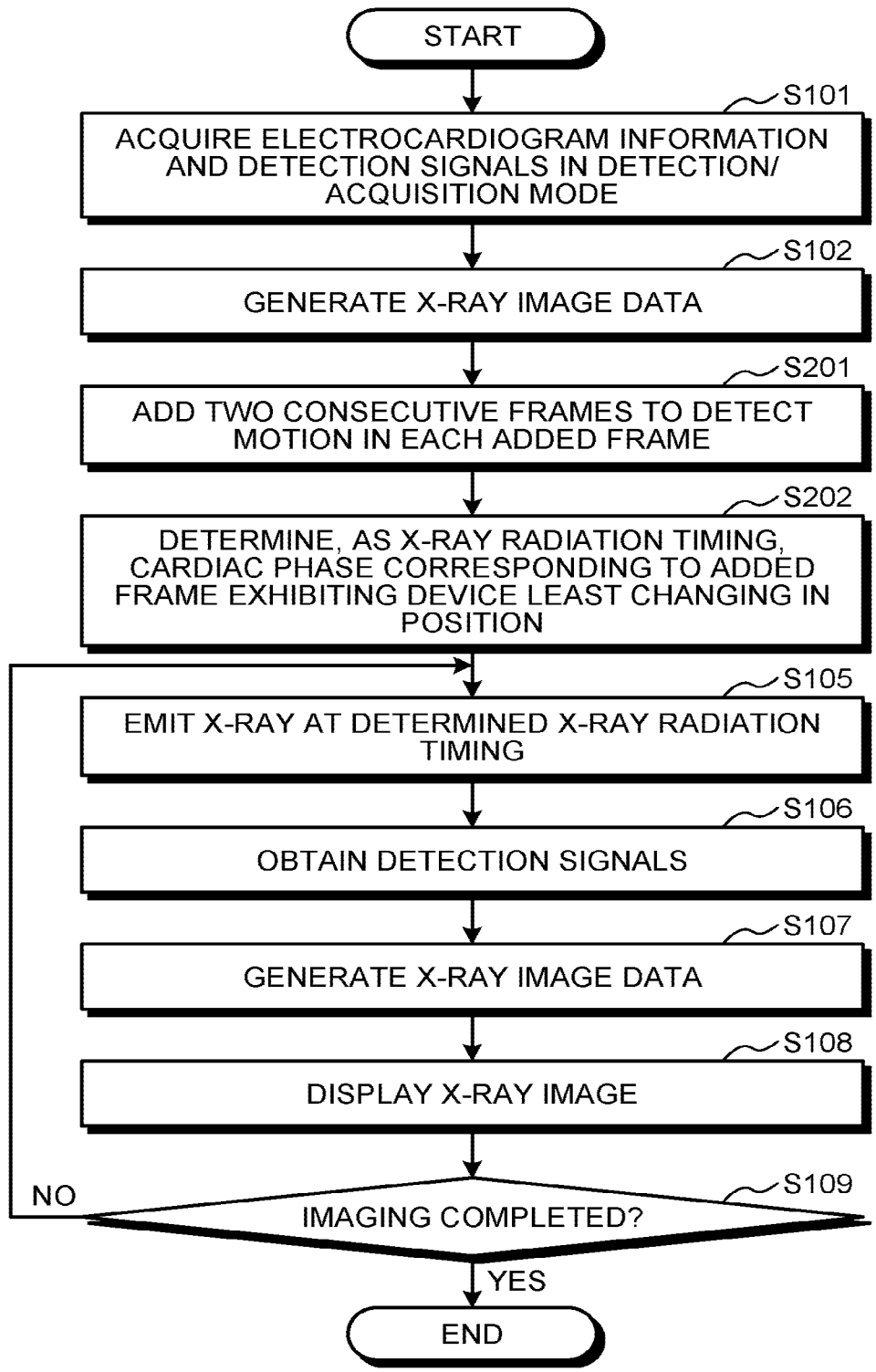
FIG. 11 is a flowchart illustrating an exemplary procedure of determining X-ray radiation timing and ECG gated imaging according to the seventh embodiment.

FIG. 11 is a flowchart illustrating an exemplary procedure of determining the X-ray radiation timing and the ECG gated imaging according to the seventh embodiment. In the flowchart, the detection/acquisition mode is assumed to be selected.

The acquisition of the electrocardiogram information in S101 is similar to that in the first embodiment. The detection signals are acquired at a higher rate than in the general imaging mode. The generation of the X-ray image data 51 in S102 is similar or same as in the first embodiment.

The detection function 213 adds every two consecutive frames among the frames 511, 512, 513, and 514 of the X-ray image data 51 to detect the motion of the device 9 from each of the added frames 551, 552, 553 (S201).

The determining function 214 determines, as the first radiation timing, a cardiac phase corresponding to the added frame 553 exhibiting the device 9 least changing in position (S202).

The processing from the X-ray radiation in S105 to the determination as to completion of the imaging in S109 is similar or same as in the first embodiment.

As such, the X-ray diagnosis apparatus 10 of the present embodiment adds every two chronologically adjacent frames among the frames 511, 512, 513, and 514 of the X-ray image data 51 to detect a change in position of the device 9 rendered in the two chronologically adjacent frames from the added frames 551, 552, 553. Thus, the X-ray diagnosis apparatus 10 of the present embodiment adopts a different detection method from the one in the first embodiment to be able to exert similar or same effects as the apparatus 10 of the first embodiment.

Eighth Embodiment

The first embodiment has described an example that the device motion rendered in the frames of the X-ray image data 50 is detected on a frame basis. In an eighth embodiment, a change in position of the device is detected from the frames of X-ray image data corresponding to two cycles of the electrocardiographic waveform 8 of the subject P, as an example.

As in the first embodiment, a system S in the present embodiment includes an X-ray diagnosis apparatus 10 and an electrocardiograph 30. As in the first embodiment, the X-ray diagnosis apparatus 10 in the present embodiment includes an X-ray high voltage apparatus 11, an X-ray tube 12, an X-ray diaphragm 13, a table top 14, a C-arm 15, an X-ray detector 16, a C-arm rotating/moving mechanism 17, a table top moving mechanism 18, a C-arm/table top control circuitry 19, diaphragm control circuitry 20, processing circuitry 21, an input interface 22, a display 23, memory circuitry 24, and device interface circuitry 25.

As in the first embodiment, the processing circuitry 21 of the X-ray diagnosis apparatus 10 includes an obtaining function 211, a generation function 212, a detection function 213, a determining function 214, an X-ray radiation control function 215, a display control function 216, and a reception function 217.

The obtaining function 211, the generation function 212, the display control function 216, and the reception function 217 include similar or same functions as those in the first embodiment.

Figure 12:
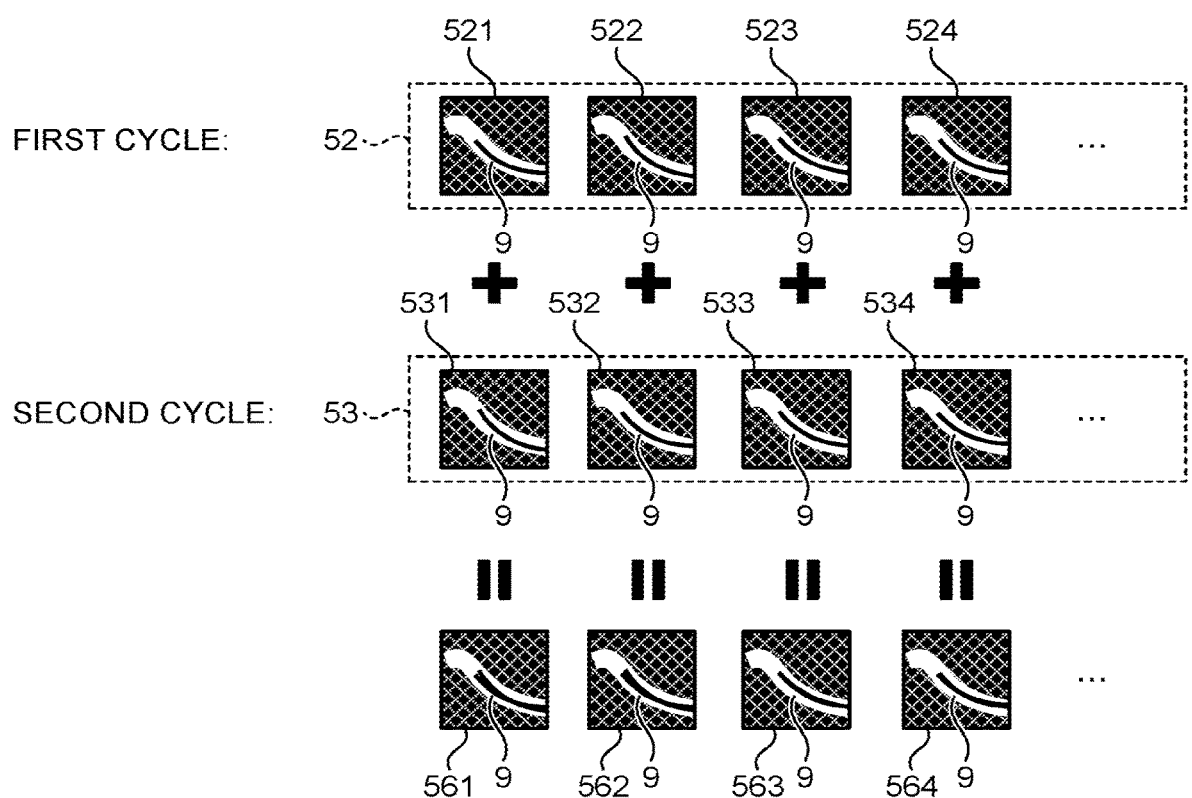
FIG. 12 illustrates an exemplary detection method of the magnitude of device motion in multiple frames included in X-ray image data according to an eighth embodiment.

FIG. 12 illustrates an exemplary detection method of the magnitude of motion of the device 9 in frames 521, 522, 523, 524, 531, 532, 533, and 534 of two pieces of X-ray image data 52 and 53 according to an eighth embodiment. The number of frames shown in FIG. 12 is merely exemplary and not to be construed as limiting.

The frames 521, 522, 523, 524, 531, 532, 533, and 534 base on the detection signals of X-rays emitted in a time series in the motion detection phase. The frames 521, 522, 523, 524, 531, 532, 533, and 534 are captured in the detection/imaging mode.

According to the present embodiment, in the detection/imaging mode the X-rays are emitted in synchronization with the cycle of the electrocardiographic waveform 8 of the subject P by ECG gated acquisition. In the detection/imaging mode the X-rays are emitted twice or more per cycle. The detection signals are acquired at a higher rate in the detection/imaging mode than in the general imaging mode. The detection/imaging mode differs from the ECG gated imaging mode to be used in the imaging phase in that a length of time from a start of the cycle of the electrocardiographic waveform 8 to each X-ray radiation timing is defined by a predetermined proportion relative to the cycle length. For example, the value of X in Equation (1) in the first embodiment is predefined in the detection/imaging mode.

Alternatively, X-rays may be emitted twice or more at predetermined intervals in one cycle in the detection/imaging mode.

In the present embodiment, among the frames 521, 522, 523, 524, 531, 532, 533, and 534 of the two pieces of X-ray image data 52 and 53 corresponding to two cycles of the electrocardiographic waveform 8 of the subject P, the detection function 213 adds two frames corresponding to the same cardiac phase of the two cycles.

Specifically, the detection function 213 adds the frame 521 and the frame 531 captured in the same cardiac phase of the first cycle and the second cycle, respectively. The frames added are referred to as an added frame 561. Likewise, the detection function 213 adds the frame 522 captured in the first cycle and the frame 532 captured in the second cycle, adds the frame 523 captured in the first cycle and the frame 533 captured in the second cycle, and adds the frame 524 captured in the first cycle and the frame 534 captured in the second cycle.

The detection function 213 detects a change in position of the device 9 rendered in the two frames corresponding to the same cardiac phase of the two cycles from the added frames 561, 562, 563, and 564. For example, a difference in position of the device 9 appearing in the two frames 521, 531 may cause a motion blur and the device 9 may appear double in the added frame 561. The detection function 213 detects the magnitude of the motion of the device 9 appearing in each of the added frame 561, 562, 563, and 563 through image processing.

In the example of FIG. 12, among the added frames 561, 562, 563, and 564, the device 9 rendered is least moving in the added frame 563. The magnitude of the motion detected by the detection function 213 may be represented in, for example, numerical values.

In the present embodiment the determining function 214 determines, as the first radiation timing, the cardiac phase corresponding to the added frame 563 exhibiting the device 9 least changing in position as detected by the detection function 213, in addition to including similar or same functions as in the first embodiment.

The cardiac phase corresponding to the added frame 563 exhibiting the device 9 least changing in position is, for example, the X-ray radiation timing for the two frames 523 and 533 on which the added frame 563 bases.

In the present embodiment the X-ray radiation control function 215 performs ECG gating and acquires the detection signals at a higher rate for imaging in the detection/imaging mode than in the general imaging mode, in addition to including similar or same functions as in the first embodiment. The general imaging mode without ECG gating and the ECG gated imaging mode are similar or same as in the first embodiment.

Figure 13:
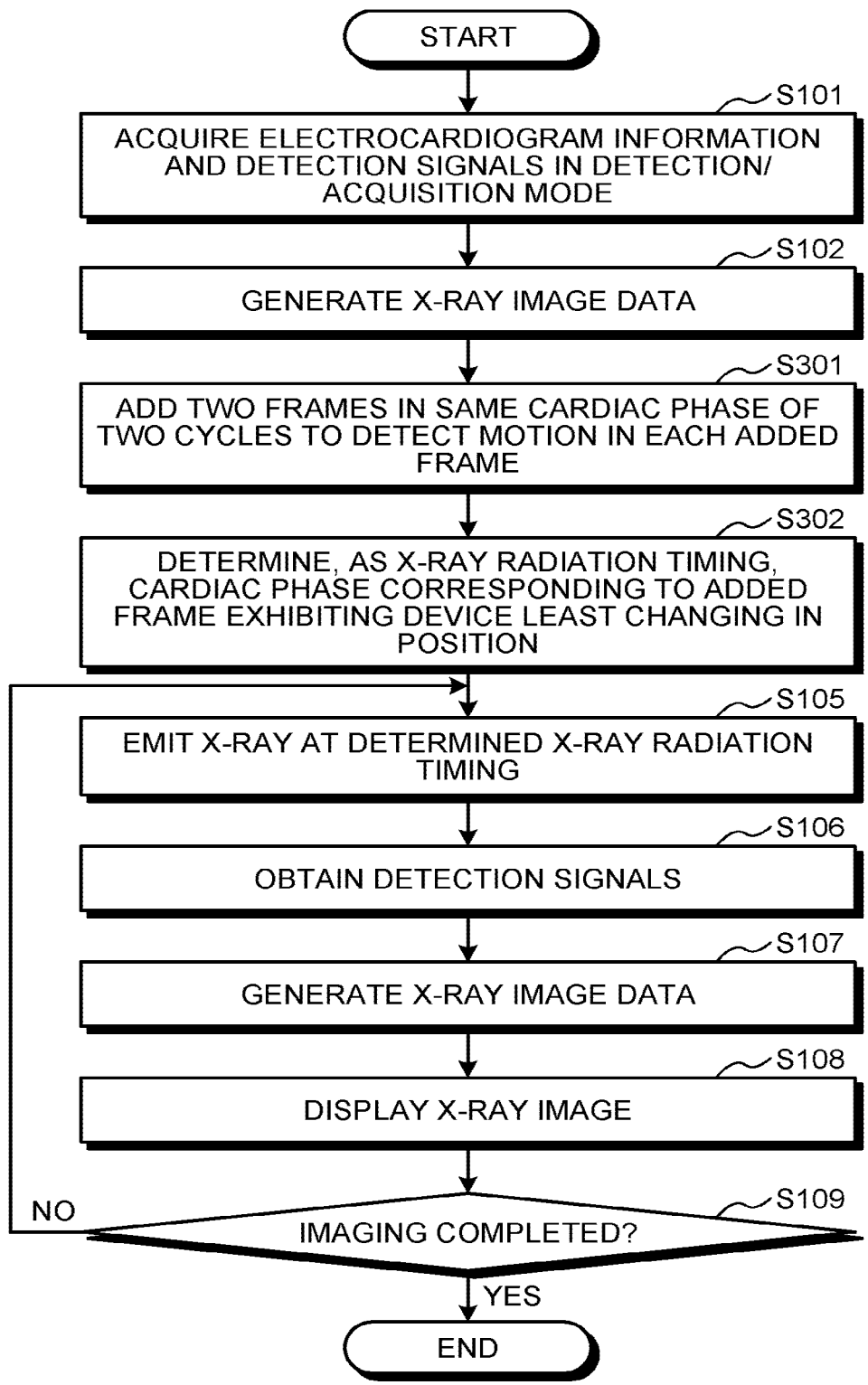
FIG. 13 is a flowchart illustrating an exemplary procedure of determining X-ray radiation timing and ECG gated imaging according to the eighth embodiment.

FIG. 13 is a flowchart illustrating an exemplary procedure of determining the X-ray radiation timing and the ECG gated imaging according to the eighth embodiment. In the flowchart, the detection/acquisition mode is assumed to be selected.

The acquisition of the electrocardiogram information in S101 is similar to that in the first embodiment. The detection signals are acquired in synchronization with the ECG at a higher rate than in the general imaging. Further, the electrocardiogram information and the detection signals corresponding to two cycles are acquired in S101 in the present embodiment. The generation of the X-ray image data 51 in S102 is similar or same as in the first embodiment.

The detection function 213 adds each two frames in the same cardiac phase of the two cycles to detect motion of the device from each of the added frames 561, 562, 563, and 564 (S301).

The determining function 214 determines, as the first radiation timing, a cardiac phase corresponding to the added frame 563 exhibiting the device 9 least changing in position (S302).

The processing from the X-ray radiation in S105 to the determination as to completion of the imaging in S109 is similar or same as in the first embodiment.

As such, in the present embodiment, among the frames 521, 522, 523, 524, 531, 532, 533, and 534 of the two pieces of X-ray image data 52, 53 corresponding to two cycles of the electrocardiographic waveform 8 of the subject P, the X-ray diagnosis apparatus 10 adds each two frames corresponding to the same cardiac phase of the two cycles to detect a change in position of the device 9 rendered in the two frames corresponding to the same cardiac phase of the two cycles from each of the added frames. Thus, the X-ray diagnosis apparatus 10 of the present embodiment adopts a different detection method from the method in the first embodiment to be able to exert similar or same effects as the apparatus 10 of the first embodiment.

First Modification

According to any of the first to eighth embodiments, the X-ray diagnosis apparatus 10 includes one display 23. The X-ray diagnosis apparatus 10 may include two or more displays 23. Alternatively, the X-ray diagnosis apparatus 10 may be connected to an external display device provided separately from the X-ray diagnosis apparatus 10.

In any of the second to sixth embodiments, for example, the subject P is irradiated with X-rays twice or more during one cycle of the electrocardiographic waveform 8 of the subject P. In such a case, among the frames of X-ray image data captured in the imaging phase, the display control function 216 may separately display a frame corresponding to the detection signal of X-rays emitted at the first radiation timing on a different display from the rest of the frames. The display control function 216 separately displays the frame corresponding to the first radiation timing and the frames corresponding to the other radiation timings in the ECG gated imaging mode.

The first radiation timing is a radiation timing corresponding to the frame 503 exhibiting the device 9 least moving among the frames of the X-ray image data 50 as detected on a frame basis in the motion detection phase, as described in the first embodiment.

Second Modification

According to the fourth and fifth embodiments, the user manipulates the tub 71 to designate the X-ray radiation timing, however, the designation method of the X-ray radiation timing is not limited thereto. As an example, the user may be allowed to click any point on the electrocardiogram 230, and the reception function 217 may receive such a click operation as a designation of the X-ray radiation timing.

Throughout the disclosure herein, various kinds of data presented are typically digital data.

According to at least one of the above-described embodiments, it is possible to irradiate the subject P with X-rays at good timing in line with the cardiac cycle of the subject P in the ECG gated X-ray imaging.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit scope of the invention as defined by the appended claims. The accompanying claims and their equivalents are intended to cover such forms or modifications as would fall within the scope and spirit of the inventions.

What is claimed is:

1. An X-ray diagnosis apparatus, comprising:
processing circuitry configured to:
obtain an electrocardiographic waveform of a subject and a detection signal;
generate X-ray image data of the subject from the obtained detection signal such that the generated X-ray image data is associated with the obtained electrocardiographic waveform based on a predetermined time;
detect motion of an object rendered in each of a plurality of frames of the generated X-ray image data;
determine a first radiation timing as a cardiac phase corresponding to one of the frames exhibiting the object least moving; and
repeatedly irradiate the subject with an X-ray at the first radiation timing in each cycle of the electrocardiographic waveform of the subject.

2. The X-ray diagnosis apparatus according to claim 1, wherein the processing circuitry is further configured to:
display a graph, the electrocardiographic waveform of the subject, and an operative element on a display in association with one another, the graph representing a magnitude of motion in each of the frames included in the X-ray image data, the operative element allowing a user to at least either change the first radiation timing or add another radiation timing, and
receive at least either a change or an addition made by the user with the operative element.

3. The X-ray diagnosis apparatus according to claim 2, wherein the processing circuitry is further configured to display at least either the graph or the electrocardiographic waveform on the display in association with at least one of the first radiation timing and an end-systolic phase and a mid-diastolic phase of the electrocardiographic waveform.

4. The X-ray diagnosis apparatus according to claim 1, wherein the processing circuitry is further configured to:
display a plurality of X-ray images based on the plurality of frames included in the X-ray image data and the electrocardiographic waveform of the subject on a display in association with each other, and
receive at least either a change of the first radiation timing or an addition of another radiation timing made by a user with reference to the electrocardiographic waveform.

5. The X-ray diagnosis apparatus according to claim 4, wherein the processing circuitry is further configured to display the electrocardiographic waveform on the display in association with at least one of the first radiation timing and an end-systolic phase and a mid-diastolic phase of the electrocardiographic waveform.

6. The X-ray diagnosis apparatus according to claim 1, wherein the processing circuitry is further configured to:
detect a change in position of a device rendered in each pair of two chronologically adjacent frames among the plurality of frames included in the generated X-ray image data, and
add the two chronologically adjacent frames of each pair to generate added frames, and
determine, as the first radiation timing, a cardiac phase corresponding to an added frame exhibiting the device least changing in position among the added frames.

7. The X-ray diagnosis apparatus according to claim 1, wherein the processing circuitry is further configured to:
detect a change in position of a device rendered in each pair of two frames corresponding to a same cardiac phase of two cycles of the electrocardiographic waveform of the subject among the plurality of frames included in the generated X-ray image data corresponding to the two cycles, and
add the two frames of each pair corresponding to the same cardiac phase to generate added frames, and
determine, as the first radiation timing, a cardiac phase corresponding to an added frame exhibiting the device least changing in position among the added frames.

8. The X-ray diagnosis apparatus according to claim 1, wherein the processing circuitry is further configured to:
display a graph, the electrocardiographic waveform of the subject, and an operative element on a display in association with one another, the graph representing a magnitude of motion in each of the frames included in the generated X-ray image data, the operative element that allows a user to at least either change the first radiation timing or add another radiation timing, and
receive at least either a change or an addition made by the user with the operative element.

9. The X-ray diagnosis apparatus according to claim 1, wherein the processing circuitry is further configured to:
display a plurality of X-ray images, based on the plurality of frames included in the generated X-ray image data, and the electrocardiographic waveform of the subject on a display in association with each other, and
receive at least either a change of the first radiation timing or an addition of another radiation timing made by a user with reference to the electrocardiographic waveform.

10. The X-ray diagnosis apparatus according to claim 1, wherein the processing circuitry is further configured to:
detect motion of a device rendered in the plurality of frames included in the generated X-ray image data on a frame basis, and
determine, as the first radiation timing, a cardiac phase corresponding to a frame exhibiting the device least moving as detected among the plurality of frames of the generated X-ray image data.

11. The X-ray diagnosis apparatus according to claim 1, wherein the processing circuitry is further configured to:
    detect a change in position of a device rendered in each pair of two chronologically adjacent frames among the plurality of frames included in the generated X-ray image data, and
    add the two chronologically adjacent frames of each pair to generate added frames, and
    determine, as the first radiation timing, a cardiac phase corresponding to an added frame exhibiting the device least changing in position among the added frames.

12. The X-ray diagnosis apparatus according to claim 1, wherein the processing circuitry is further configured to:
    detect a change in position of a device rendered in each pair of two frames corresponding to a same cardiac phase of two cycles of the electrocardiographic waveform of the subject among the plurality of frames included in the generated X-ray image data corresponding to the two cycles, and
    add the two frames of each pair corresponding to the same cardiac phase to generate added frames, and
    determine, as the first radiation timing, a cardiac phase corresponding to an added frame exhibiting the device least changing in position among the added frames.

13. The X-ray diagnosis apparatus according to claim 1, wherein the processing circuitry is further configured to determine a predetermined number of X-ray radiation timings per cycle of the electrocardiographic waveform of the subject, in addition to the first radiation timing.

14. The X-ray diagnosis apparatus according to claim 1, further comprising an X-ray detector configured to accumulate and read electric charge in a regular cycle,
    wherein the processing circuitry is further configured to adjust the first radiation timing or another radiation timing in line with a charge accumulation period of the X-ray detector.

15. An X-ray diagnosis apparatus comprising:
    processing circuitry configured to:
    obtain an electrocardiographic waveform of a subject and a detection signal;
    generate X-ray image data of the subject from the obtained detection signal such that the generated X-ray image data is associated with the obtained electrocardiographic waveform based on a predetermined time;
    detect motion of an object rendered in each of a plurality of frames of the generated X-ray image data;
    display a graph, the electrocardiographic waveform of the subject, and an operative element on a display in association with one another such that time axes of the graph, the electrocardiographic waveform, and the operative element match each other, the graph representing a magnitude of the motion in each of the plurality of frames included in the generated X-ray image data of the subject, the operative element allowing a user to designate an X-ray radiation timing with respect to the subject, and
    receive the X-ray radiation timing designated by the user through a manipulation of the operative element to designate a time on the time axes.

16. The X-ray diagnosis apparatus according to claim 15, wherein the processing circuitry is further configured to display at least either the graph or the electrocardiographic waveform on the display in association with at least one of the X-ray radiation timing and an end-systolic phase and a mid-diastolic phase of the electrocardiographic waveform.

17. An X-ray diagnosis apparatus comprising:
    processing circuitry configured to:
    obtain an electrocardiographic waveform of a subject and a detection signal;
    generate X-ray image data of the subject from the obtained detection signal such that the generated X-ray image data is associated with the obtained electrocardiographic waveform based on a predetermined time;
    display, on a display, a plurality of X-ray images based on a plurality of frames included in the generated X-ray image data of the subject and the electrocardiographic waveform of the subject in association with each other such that an X-ray image at a time indicated in the electrocardiographic waveform is displayed, and
    receive a designation of an X-ray radiation timing with respect to the subject made by a user designating a time on a time axis of the electrocardiographic waveform with reference to the electrocardiographic waveform.

18. The X-ray diagnosis apparatus according to claim 17, wherein the processing circuitry is further configured to display the electrocardiographic waveform on the display in association with at least one of the X-ray radiation timing and an end-systolic phase and a mid-diastolic phase of the electrocardiographic waveform.

* * * * *